(12) United States Patent
Soon-Shiong

(10) Patent No.: US 10,580,523 B2
(45) Date of Patent: *Mar. 3, 2020

(54) HEALTHCARE ANALYSIS STREAM MANAGEMENT

(71) Applicant: Nant Holdings IP, LLC, Culver City, CA (US)

(72) Inventor: Patrick Soon-Shiong, Los Angeles, CA (US)

(73) Assignee: Nant Holdings IP, LLC, Culver City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/124,076

(22) Filed: Sep. 6, 2018

(65) Prior Publication Data

US 2019/0006028 A1 Jan. 3, 2019

Related U.S. Application Data

(63) Continuation of application No. 15/362,653, filed on Nov. 28, 2016, now Pat. No. 10,095,835, which is a
(Continued)

(51) Int. Cl.
| | |
|---|---|
| *G01N 33/48* | (2006.01) |
| *G01N 33/50* | (2006.01) |
| *G16H 10/60* | (2018.01) |
| *G16B 20/00* | (2019.01) |
| *G16B 30/00* | (2019.01) |

(Continued)

(52) U.S. Cl.
CPC ............ *G16H 10/60* (2018.01); *G06F 19/00* (2013.01); *G06F 19/321* (2013.01); *G06F 19/324* (2013.01); *G16B 20/00* (2019.02); *G16B 30/00* (2019.02); *G16B 50/00* (2019.02); *G16H 30/20* (2018.01); *G16H 40/00* (2018.01); *G16H 70/00* (2018.01); *H04L 67/10* (2013.01); *H04L 67/42* (2013.01)

(58) Field of Classification Search
None
See application file for complete search history.

(56) References Cited

U.S. PATENT DOCUMENTS

| | | |
|---|---|---|
| 5,132,842 A | 7/1992 | Yeh |
| 5,555,366 A | 9/1996 | Teig et al. |

(Continued)

FOREIGN PATENT DOCUMENTS

| | | |
|---|---|---|
| CN | 201294149 Y | 8/2009 |
| CN | 102521529 A | 6/2012 |

(Continued)

OTHER PUBLICATIONS

Vaske et al. Inference of patient-specific pathway activities from multi-dimensional cancer genomics data using Paradigm. Bioinformatics, vol. 26, pp. i237-i245. (Year: 2010).*

(Continued)

*Primary Examiner* — Russell S Negin
(74) *Attorney, Agent, or Firm* — Mauriel Kapouytian Woods LLP; Michael Mauriel; Andrew A. Noble

(57) ABSTRACT

Apparatus, systems and methods for pre-processing, analyzing, and storing genomic data through a scalable, distributed analysis system across a network is presented.

25 Claims, 7 Drawing Sheets

Related U.S. Application Data continuation of application No. 13/935,371, filed on Jul. 3, 2013, now Pat. No. 9,953,137.

(60) Provisional application No. 61/842,325, filed on Jul. 2, 2013, provisional application No. 61/842,323, filed on Jul. 2, 2013, provisional application No. 61/842,316, filed on Jul. 2, 2013, provisional application No. 61/673,943, filed on Jul. 20, 2012, provisional application No. 61/668,941, filed on Jul. 6, 2012.

(51) Int. Cl.
*G16B 50/00* (2019.01)
*G06F 19/00* (2018.01)
*G16H 70/00* (2018.01)
*G16H 30/20* (2018.01)
*G16H 40/00* (2018.01)
*H04L 29/08* (2006.01)
*H04L 29/06* (2006.01)

(56) References Cited

U.S. PATENT DOCUMENTS

| | | |
|---|---|---|
| 6,909,700 B1 | 6/2005 | Benmohamed et al. |
| 7,996,186 B2 | 8/2011 | Nakagawa et al. |
| 8,446,593 B1 | 5/2013 | Ellerbee |
| 9,953,137 B2 | 4/2018 | Soon-Shiong |
| 10,055,546 B2 | 8/2018 | Soon-Shiong |
| 10,095,835 B2 | 10/2018 | Soon-Shiong |
| 2001/0051879 A1 | 12/2001 | Johnson et al. |
| 2003/0129603 A1 | 7/2003 | Wolffe et al. |
| 2003/0175782 A1 | 9/2003 | Fukushima et al. |
| 2004/0197797 A1 | 10/2004 | Inoko et al. |
| 2005/0069874 A1 | 3/2005 | Yasuda et al. |
| 2005/0149360 A1 | 7/2005 | Galperin |
| 2005/0191731 A1 | 9/2005 | Judson et al. |
| 2005/0210044 A1 | 9/2005 | Hills et al. |
| 2005/0260663 A1 | 11/2005 | Solomon |
| 2006/0147087 A1 | 7/2006 | Goncalves et al. |
| 2006/0226957 A1 | 10/2006 | Miller et al. |
| 2006/0293925 A1 | 12/2006 | Flom |
| 2007/0239482 A1 | 10/2007 | Finn et al. |
| 2008/0004904 A1 | 1/2008 | Tran |
| 2008/0077607 A1 | 3/2008 | Gatawood et al. |
| 2008/0082503 A1 | 4/2008 | Jung et al. |
| 2008/0147554 A1 | 6/2008 | Stevens et al. |
| 2008/0228410 A1 | 9/2008 | Kenedy et al. |
| 2008/0281529 A1 | 11/2008 | Tenenbaum et al. |
| 2008/0281530 A1 | 11/2008 | Tenenbaum et al. |
| 2008/0281818 A1 | 11/2008 | Tenenbaum et al. |
| 2008/0281819 A1 | 11/2008 | Tenenbaum et al. |
| 2009/0005650 A1 | 1/2009 | Angell et al. |
| 2009/0006125 A1 | 1/2009 | Angell et al. |
| 2009/0150084 A1 | 6/2009 | Colwell et al. |
| 2009/0227876 A1 | 9/2009 | Tran |
| 2009/0227877 A1 | 9/2009 | Tran |
| 2009/0299645 A1 | 12/2009 | Colby et al. |
| 2009/0318779 A1 | 12/2009 | Tran |
| 2010/0105034 A1 | 4/2010 | Hutton et al. |
| 2010/0137166 A1 | 6/2010 | Kain et al. |
| 2010/0211371 A1 | 8/2010 | Kim et al. |
| 2011/0070587 A1 | 3/2011 | Fuernkranz et al. |
| 2011/0091880 A1 | 4/2011 | Rafnar et al. |
| 2011/0115624 A1 | 5/2011 | Tran |
| 2011/0125519 A1 | 5/2011 | Dhoble |
| 2011/0125521 A1 | 5/2011 | Dhoble |
| 2011/0181422 A1 | 7/2011 | Tran |
| 2012/0004111 A1 | 1/2012 | Colwell et al. |
| 2012/0041683 A1* | 2/2012 | Vaske .................. G16B 5/00 702/19 |
| 2012/0059670 A1 | 3/2012 | Sanborn et al. |
| 2012/0066001 A1 | 3/2012 | Sanborn et al. |
| 2012/0143622 A1 | 6/2012 | Oesterheld et al. |
| 2012/0322675 A1 | 12/2012 | Gilbert et al. |
| 2013/0013623 A1 | 1/2013 | Shah et al. |
| 2014/0249847 A1 | 9/2014 | Soon-Shiong et al. |

FOREIGN PATENT DOCUMENTS

| | | |
|---|---|---|
| GB | 2 403 041 A | 12/2004 |
| JP | 2001167072 A | 6/2001 |
| JP | 2002153271 A | 5/2002 |
| JP | 2002183153 A | 6/2002 |
| JP | 2004147640 A | 5/2004 |
| JP | 2011238252 A | 11/2011 |
| WO | WO 00/15847 A2 | 3/2000 |
| WO | WO 01/43051 A2 | 6/2001 |
| WO | WO 02/44967 A1 | 6/2002 |
| WO | WO 02/093453 A2 | 11/2002 |
| WO | WO 2006/116455 A2 | 11/2006 |
| WO | WO 2009/085473 A2 | 7/2009 |
| WO | WO 2011/139345 A2 | 11/2011 |
| WO | WO 2011/149534 A2 | 12/2011 |
| WO | WO 2013/052937 A1 | 4/2013 |
| WO | WO 2013/062505 A1 | 5/2013 |
| WO | WO 2013/074058 A1 | 5/2013 |
| WO | WO 2013/086355 A1 | 6/2013 |
| WO | WO 2013/086424 A1 | 6/2013 |

OTHER PUBLICATIONS

Hallam, "Oxford Nanopore to Sell Tiny DNA Sequencer," Bloomberg, Feb. 17, 2012, 4 pages.

Pollack, "Company Unveils DNA Sequencing Device Meant to Be Portable, Disposable and Cheap," The New York Times, Feb. 17, 2012, 3 pages.

Park et al., "New Concept for Fast, Low-Cost DNA Sequencing Device," Science Daily, Apr. 24, 2012, 3 pages.

"National Lambda Rail," Network for Advanced Research and Innovation, www.nlr.net, 2 pages.

Schlessinger et al., "Structure-based discovery of prescription drugs that interact with the norepinephrine transporter, NET," PNAS, vol. 108, No. 38, Sep. 20, 2011, pp. 15810-15815.

Tu et al., "Efficient SDH Computation in Molecular Simulations Data," BCB '12 Proceedings of the ACM Conference on Bioinformatics, Computational Biology and Biomedicine, pp. 527-529.

Anderson et al., "General purpose molecular dynamics simulations fully implemented on graphics processing units," Journal of Computational Physics, vol. 227, 2008, pp. 5342-5359.

Stone et al., "GPU-Accelerated Molecular Modeling Come of Age," J Mol Graph Model, Sep. 2010, 20 pages.

Sukhwani et al., "GPU Acceleration of a Production Molecular Docking Code," GPGPU-2 Proceedings of 2nd Workshop on General Purpose Processing on Graphics Processing Units, 9 pages.

Rodrigues et al., "GPU Acceleration of Cutoff Pair Potentials for Molecular Modeling Applications," CF '08 Proceedings of the 5th conference on Computing frontiers, 2008, pp. 273-282.

Wu et al., "A GPU-Based Approach to Accelerate Computational Protein-DNA Docking," Computing in Science and Engineering, vol. 14, Issue 3, pp. 20-28.

Shoichet et al., "Lead discovery using molecular docking," Current Opinion in Chemical Biology, vol. 6, Issue 4, Aug. 2002, pp. 439-446.

"Molegro Virtual Docker—High Accuracy Molecular Docking," CLC bio, Product Datasheet, http://www.clcbio.com/files/productsheets/MolegroVirtualDocker.pdf, 4 pages.

Sherman Patent Search Group, Project: Molecular Docking System, Jun. 17, 2013, 7 pages.

Ritchie, "Ultra-fast FFT protein docking on graphics processors," Bioinformatics, vol. 26, No. 19, 2010, pp. 2398-2405.

Ma et al., "Molecular docking for virtual screening of natural product databases," Chemical Science, Issue 9, 2011, pp. 1656-1665.

International Search Report and Written Opinion for International Application No. PCT/US2013/049383 dated Dec. 9, 2013, 10 pages.

(56) References Cited

OTHER PUBLICATIONS

Estrada et al., "Local Features Tutorial," http://www.cs.toronto.edu/-jepson/csc2503/tutSIFT04.pdf, Nov. 8, 2004, pp. 1-25.
Jalali et al., "Time-Stretch Imaging and its Applications to High-throughput Microscopy and Microsurgery," IEEE Photonics Society News, vol. 24, No. 3, Jun. 2010, pp. 10-15.
Goda et al., "Serial time-encoded amplified imaging for real-time observation of fast dynamic phenomena," Nature, vol. 458, Apr. 30, 2009, pp. 1145-1150.
Jalali et al., "Breaking Speed and Sensitivity Limits Real-Time Diagnostics with Serial Time-Encoded Amplified Microscopy," Ultrafast Imaging, Optik & Photonik, No. 2, Jun. 2010, pp. 32-36.
Fard et al., "Nomarski serial time-encoded amplified microscopy for high-speed contrast-enhanced imaging of transparent media," Biomedical Optics Express, vol. 2, No. 12, pp. 3387-3392.
Keim, "Fastest Camera Ever Built Uses Lasers," Wired, www.wired.com/wiredscience/2009/04/fastestcamera/, Apr. 29, 2009, 8 pages.
Zhang et al., "Serial time-encoded amplified microscopy (STEAM) based on a stabilized picosecond super-continuum source," Optics Express, vol. 19. No. 17, Aug. 15, 2011, pp. 15310-15816.
Fitzhugh, "NantWorks Delivers High-Speed Genomics Platform," The Burrill Report, The Journal of Life Sciences, Oct. 4, 2012, 2 pages.
Sedgewick et al., "Learning Subgroup-Specific Regulatory Interactions and Regulator Independence with Paradigm," Bioinformatics, vol. 29, 2013, pp. i62-i70.
Extended European Search Report issued in European Patent Application No. 13812807.9 dated Feb. 5, 2016, 8 pages.
International Search Report and Written Opinion issued for International Application No. PCT/US2012/059155 dated Dec. 27, 2012, 3 pages.
Lowe, "Object Recognition from Local Scale-Invariant Features," Computer Vision, Sep. 1999, pp. 1-8.
Gardner et al., "Parallel genomic sequence-searching on an ad-hoc grid: experiences, lessons learned, and implications," Proceedings of the 2006 ACM/IEEE SC/06 Conference, IEEE Computer Society, 14 pages.
Harris, "Genotator: A workbench for sequence annotation," Genome Research, 1997, vol. 7, pp. 754-762.
Binladen et al., "The Use of Coded PCR Primers Enables High-Throughput Sequencing of Multiple Hornolog Amplification Products by 454 Parallel Sequencing." PLoS ONE, 2007, Issue 2, Article e197, 9 pages.
Examination Report issued in Australian Application No. 2013286622 dated Jul. 17, 2018, 3 pages.
Office Action issued in European Application No. 13 812 807.9 dated Feb. 7, 2018, 10 pages.
Examination Report issued in Australian Application No. 2013286622 dated Dec. 18, 2017, 3 pages.
Office Action issued in Japanese Patent Application No. 2015-520695 dated Aug. 29, 2017, 6 pages.
Office Action issued in Chinese Patent Application No. 201380038252.7 dated May 2, 2017, 4 pages.
Office Action issued in Japanese Patent Application No. 2015-520695 dated Apr. 18, 2018, 8 pages.
Office Action issued in Chinese Patent Application No. 201380038252.7 dated Dec. 21, 2017, 8 pages.
Office Action issued in Canadian Patent Application No. 2,878,455 dated Oct. 31, 2018, 4 pages.
Office Action issued in Korean Patent Application No. 10-2015-7002523 dated Apr. 25, 2019, 10 pages.
Krampis et al., "Cloud BioLinux: pre-configured and on-demand bioinformatics computing for the genomics commmunity," BMC Bioinformatics, 2012, vol. 13, 8 pages.
Office Action issued in Chinese Patent Application No. 201380038252.7 dated Jan. 16, 2019, 6 pages.
Office Action issued in Japanese Patent Application No. 2017-251135 dated Feb. 19, 2019, 3 pages.
Office Action issued in Korean Application No. 10-2015-7002523 dated Oct. 28, 2019, 10 pages.
Orvis et al., "Ergatis: a web interface and scalable software system for bioinformatics workflows," Bioinformatics, 2010, vol. 26, No. 12, pp. 1488-1492.

\* cited by examiner

National LambdaRail (see URL www(dot)nlr(dot)net/docs/NLR_OverviewBrochure.pdf).

HEALTHCARE ANALYSIS STREAM MANAGEMENT

This application is a continuation of U.S. non-provisional application having Ser. No. 15/362,653 filed Nov. 28, 2016, which is a continuation of U.S. non-provisional application having Ser. No. 13/935,371 filed Jul. 3, 2013, which claims the benefit of priority to U.S. provisional application having Ser. No. 61/668,941 filed Jul. 6, 2012; U.S. provisional application having Ser. No. 61/673,943, filed Jul. 20, 2012; and U.S. provisional applications having Ser. Nos. 61/842,316, 61/842,323, and 61/842,325 filed Jul. 2, 2013. This application is also related to U.S. non-provisional application having Ser. No. 15/181,301 filed Jun. 13, 2016, which is also a continuation of U.S. non-provisional application having Ser. No. 13/935,371 filed Jul. 3, 2013. These and all other extrinsic materials discussed herein are incorporated by reference in their entirety.

A portion of the diclosure of this patent document contains material which is subject to copyright protection. The copyright owner has no objection to the facsimile reproduction by anyone of the patent document of the patent disclosure, as it appears in the Patent and Trademark Office patent file or records, but otherwise reserves all copyright rights whatsoever.

FIELD OF THE INVENTION

The field of the invention is genomic analysis technologies.

BACKGROUND

As genomic analysis techniques have advanced, the ability to process the vast amount of raw sequence data has not kept pace to provide information quickly to yield prognoses, diagnoses, and other genome-based analyses to a point-of-care, a patient, or healthcare provider. Some effort has been made to produce efficient genomic analyses, but these efforts have all failed to provide this kind of analysis across a large number of data sets associated with individuals and populations.

International Application No. PCT/US2002/014665 to Hytopoulos discusses an apparatus and method for performing genetic analyses in a client-server environment over a data network. However, Hytopoulos fails to harness the advantages of large-scale or continent-wide fiber optic networks to parse out segments of genomic information for analysis in parallel.

U.S. Pat. Publ. No. 2012/0066001 A1 to Sanborn discusses a method for deriving a differential genetic sequence object on the basis of alignment of sub-strings via incremental synchronization of sequence strings using known positions of the sub-strings relative to a reference genome sequence. Sanborn, however, does not appear to discuss utilizing a plurality of analysis nodes connected on an analysis network to process sequence data from a plurality of patients in parallel.

International Application No. PCT/US1999/020449 to Steward discusses a method of genomic data discovery, by providing a gene database, selecting at least 10 genes, discovering knowledge for selected gene, repeating these steps for a plurality of genes, and repeating all steps such that knowledge is discovered substantially in parallel for all the selected genes. Steward, however, does not appear to discuss utilizing an analysis network and a plurality of analysis nodes to yield quick and efficient results at a point-of-care, a patient, or healthcare provider.

International Application No. PCT/US2000/042469 to Dyer discusses a computer search tool and supporting database for use in analyzing genomes. Dyer, however, does not appear to discuss acquiring sequence data from a plurality of sequencing devices nor utilizing a plurality of analysis nodes connected on an analysis network to process sequence data from patients in parallel.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

To date, the ability to derive actionable information from genomic analysis has been hindered equally by the inability to (1) rapidly transport big genomic data to processing and storage computers located at centralized data centers, (2) accurately assess all of the variances found in the DNA of a patient's cancer tissue, (3) identify the many clones in a heterogeneous disease such as cancer, and (4) predict the systemic impact of each variance of each clone on the cellular signaling pathways.

Thus, there is still a need for harnessing large-scale networks and continent-wide fiber-optic networks to provide genomic analysis stream management.

SUMMARY OF THE INVENTION

The inventive subject matter provides apparatuses, systems and methods in which one can use a computer/server-based system to analyze genomic data through a distributed analysis system across a network. One aspect of the inventive subject matter includes a genomic analysis system to process genomic sequence data from many patients in parallel by using a sequencing device interface, an analysis network, and a plurality of analysis nodes connected through the analysis network. The sequencing device interface can be configured to obtain sequencing data from many sequencing devices in parallel, from image recognition programs or devices, and/or one or more databases storing sequence information. The analysis nodes of the genomic analysis system can include engine management nodes, network switches, high performance computing facilities (HPCs), or genomic stream management nodes to exchange some sequence data and genome data. The genomic stream management node can be configured to manage the analysis engine based on stream management functionality. The analysis network and plurality of analysis nodes comprise the genomic analysis engine, and where desired, one or more databases storing sequence information from previous sequencing runs, reference sequences, etc. The analysis engine can process sequence data to generate genome data of individual patients or demographic of patients and compare the data against a normalized genomic sequence or a statistical sample from a population of patients. The analysis engine can also process sequence data image recognition programs or devices. The analysis network can comprises an optic fiber data link, a geographically-distributed optic fiber network, or even a continent-spanning network.

The genomic analysis system generates notifications based on genome data, processing or analysis statuses, alerts or alarms, sequence device instructions, analysis recommendations, prognoses or diagnoses, or requests for further analysis. The notification system can establish a route for a notification within the analysis network to allow the notification to be sent to a point-of-care, a sequencing device, a patient, a healthcare service provider, or some combination thereof. The analysis engine can also be configured to establish processing routes among the analysis nodes such that each node can conduct a different analysis. The processing routes (e.g., a stream route, an analysis route, a notification route, etc.) can be established as a function of an expected diagnosis, priority, urgency, sequence annotations, or other factors to balance network load. The genomic analysis system can include a management interface to allow a user to provide feedback and sequence device instructions.

Another aspect of the inventive subject matter includes an add-on module to the sequencing system to pre-analyze the raw sequence data to generate a sequence annotation as well as to assemble and forward the pre-analyzed data according to these sequence annotations to a sequence analysis facility such as a high performance computing facility. The raw sequence data can include genomic sequence data, proteomic sequence data, RNA and small RNA sequence data, and epigenetic sequence data. The sequence annotations can include various processing parameters, sequence information, or patient information. The add-on module can be configured to package the pre-analyzed sequence data in a format acceptable to the analysis facility. The add-on module can also include a licensing manager, which manages communications between the analysis facility and the add-on module. The add-on module can further include a sequence device controller that sends commands to the sequence device, based on instructions from the analysis facility. The add-on module can include a storage device controller that sends commands to a storage facility based on pre-analyzed sequence data. The add-on module can be a hardware module configured to couple with a legacy sequence device. In other embodiments, the sequence device or the analysis facility itself can function as the add-on module.

A further aspect of the inventive subject matter includes a method of pre-processing raw sequence data to provide access to an a priori knowledge base and to a pre-processing engine that receives and pre-processes raw data, associates the sequence annotation with the raw sequence data to generate pre-processed sequence data, and forwards the pre-processed sequence data to a sequence genomic analysis facility. The pre-processing method can also include a step to roughly align raw data reads against a known genomic map from the a priori knowledge base based on positions relative to and within a chromosome; associations with a known allele, marker, or mutation; or some combination thereof. This step to generate a rough alignment can be part of the sequence annotation. Sequence annotations may also include known genetic or disease markers, administrative codes, routing information, patient information, a demographic, a geographic coordinate, a chain of custody, a suspected diagnosis, an analysis prioritization, or an alert trigger. The method of pre-processing raw sequence data can further include pre-processing in-band with the analysis facility that is substantially in real-time with reception of the raw sequence data.

An additional aspect of the inventive subject matter includes an interactive sequence analysis system where one or more sequence device adapters are coupled with one or more analysis engines to bi-directionally exchange data with at least one analysis engine and target sequence device. The sequence data can be pre-processed sequence data. The sequence device adapter can comprise a plurality of sequence device adapters where each adapter targets a different type of sequencing machine so that a mix of sequencers are capable of working with a single, common core analysis engine. The analysis engine can include a distributed analysis engine having a plurality of analysis nodes, where the nodes themselves may be geographically distributed. The analysis engines are configured to submit sequencing instructions over a network or optic fiber network to the target sequencing device via the sequencing device adapter. Based on patient or disease information, the sequence instructions comprise instructions or commands to the target sequencing device and analysis engines to repeat, start, or stop sequencing; delete, send, or forward data; prioritize or schedule sequencing instructions; or give licensing management instructions.

One aspect of the inventive subject matter includes a genomic storage facility with a distributed genomic database and a genomic search engine. The genome database can store genomic data records associated with a population of patients and can be indexed by many kinds of unique, demographic, or medical identifiers. The genomic data can comprise differences between a patient's sequence and a reference sequence based on time, demographics, a normalized sequence, disease, or external factors. The genomic database can be stored in memory that is distributed across genomic analysis nodes such as high performance computing facilities over a network or optic fiber network. The genomic search engine can be configured to return records from the database in response to a natural language or machine query.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
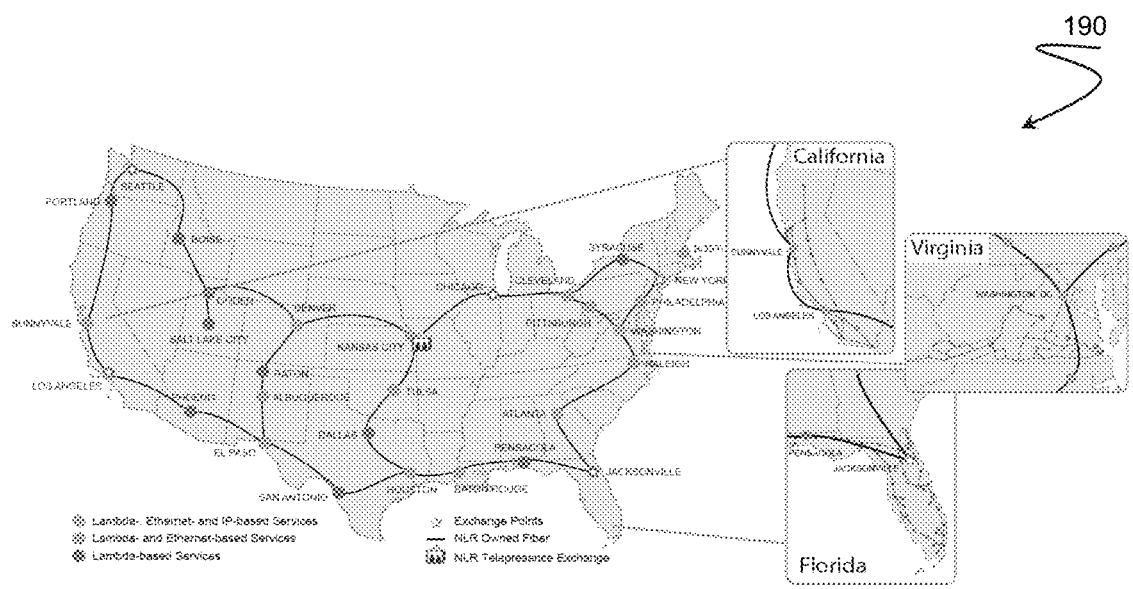
FIG. 1 is an illustration of the National LambdaRail™, which can function as the backbone for a genomic analysis system.

It should be noted that while the following description is drawn to a computer/server based genomic analysis system, various alternative configurations are also deemed suitable and may employ various computing devices including servers, interfaces, systems, databases, agents, peers, engines, modules, controllers, or other types of computing devices operating individually or collectively. One should appreciate that such terms are deemed to represent computing devices comprising at least one processor, possibly multi-core processors, configured to execute software instructions stored on a tangible, non-transitory computer readable storage medium (e.g., hard drive, solid state drive, RAM, flash, ROM, memory, distribute memory, etc.). The software instructions preferably configure or program the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

One should appreciate that the disclosed techniques provide many advantageous technical effects including generating one or more signals that configure genomic analysis devices to participate within a genomic analysis. The signals can be generated according to information derived from a genetic sequence. Further the signals can represent configuration parameters possibly including parameters affecting analysis, routing, storage, notification, license management, management, alerts, inventory, logging, reporting, security, metadata, dashboards, analysis stream flow, or other aspects of the genomic analysis.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used in the description herein and throughout the claims that follow, the meaning of "an," "an," and "the" includes plural reference unless the context clearly dictates otherwise. Also, as used in the description herein, the meaning of "in" includes "in" and "on" unless the context clearly dictates otherwise.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Further, the terms "coupled to" and "coupled with" are used euphemistically to mean "communicatively coupled with" where networked devices are able to communicate with each other over a network, possibly via one or more intermediary devices.

Overview

A preferred genomic analysis stream management system comprises a massively scalable system for pre-analyzing, annotating, or analyzing raw sequence data to produce analytical results of genomic data. The contemplated system is useful for providing immediate information available in real-time on genomic data to healthcare providers, patients, scientists, or other users. While prior techniques can take several days, weeks or months to sequence a human genome of approximately three billion base pairs and map the 20,000 to 25,000 genes, this genomic analysis system can achieve the responsiveness goal in minutes or hours. The system achieves this goal by pre-annotating raw gene data, parsing out packets of annotated gene data to a plurality of analysis nodes, running these analyses in parallel on the large-scale, continent-wide analysis network, and possibly through sending/receiving notifications to a point-of-care, a patient, healthcare provider, scientist or researcher, or other users. The efficiency and quickness of this system is due to parallel analyses operating on a plurality of analysis nodes via a high throughput network. The genomic data results can provide prognoses, diagnoses, or other analyses on the sequence data in a very timely fashion.

The genomic analysis stream management system also manages the data streams throughout the network. The management system can establish processing routes, adjust routes based on traffic or analysis load, manage the analysis engine, initiate or alter analyses, request additional analyses to gain a higher confidence level in sequence data results, or other actions to efficiently manage inputs, processes, analyses, or outputs.

Genomic data can be large-scale genetic data (e.g., static genomic information, including data on ploidy/caryotype, heterozyocity, allele frequency, etc., as well as dynamic genomic information, including time-course of changes in static information, evolutionary analysis data, etc.), data at higher resolution (e.g., genomic DNA and cDNA data for contigs, assembled contigs, chromosomes, gene-and/or disease related sequence information, partial or complete transcriptome data, RNA data of various types, including hnRNA, mRNA, snRNA, siRNA, splice variants, etc.), as well as information on group or groups of nucleic acids (e.g., codon usage, unusual nucleobases, particularly for RNA). Moreover, it should be appreciated that the genomic data may also comprise contextual information, and particularly preferred contextual information includes data related to regulatory pathways to which the sequence is subject to or participates in, wherein the regulatory pathways may be on the replicative, apoptotic, transcriptional, translational, or post-translational level. Thus, it should be noted that the information may also be relevant/associated with the activity or function of a protein product encoded by the nucleic acid sequence and/or may relate to proteomics data. In still further contemplated aspects, the genomic data may also comprise or relate to disease relevant information (e.g., sequences and/or regulatory data associated with pathogens or pathophysiology.

The distributed analysis system network can be a computer/server based genomic analysis system or any configuration of computing devices including servers, interfaces, systems, databases, agents, peers, engines, controllers, or other types of computing devices operating individually or collectively. The analysis system can have a plurality of analysis nodes, where the nodes themselves may be geographically distributed. An example of a distributed network system that can be adapted for use in the disclosed distributed genomic analysis stream management system includes the National LambdaRail™ (NLR).

Nodes can be distributed across the country in universities or federal laboratories as well as potentially international facilities to conduct analysis. The NLR has regional networks associated with its thirteen members: CENIC, Florida LambdaRail, Front Range GigaPoP/University Corporation for Atmospheric Research, Lonestar Education and Research Network, Mid-Atlantic Terascale Partnership: MATP/Virginia Tech Foundation, North Carolina Light Rail, Oak Ridge National Laboratory, Oklahoma State Regents for Higher Education, Pacific Northwest Gigapop, Pittsburgh Supercomputing Center/University of Pittsburgh, Southeastern Universities Research Association, Southern Light Rail, and University of New Mexico (on behalf of the State of New Mexico).

In FIG. 1 the National LambdaRail™ (NLR) 190 accessible by the applicant is presented.

The NLR 190 is nationwide, advanced optical network infrastructure that can function as the backbone for the contemplated distributed analysis system. The NLR 190 is a high-speed, fiber-optic network infrastructure covering 12,000 miles and 21 states across the United States. The NLR 190 does not impose any restrictions on usage, as do commercial carriers, offering users total flexibility and control. With a total capacity of 1600 Gbps, production 40G implemented, and planning underway (as of 2012) for 100G, the NLR 190 is the cutting-edge network platform for a wide range of advanced research projects and public-private partnerships. Over 280 participating universities and federal labs use the NLR 190. The NLR 190 is the first transcontinental, production 10-Gigabit Ethernet network. The NLR 190 has five international exchange points and has links to other networks throughout the world via a partnership with Global Lambda Integrated Facility.

Genomic Analysis Stream Management Systems

Figure 2:
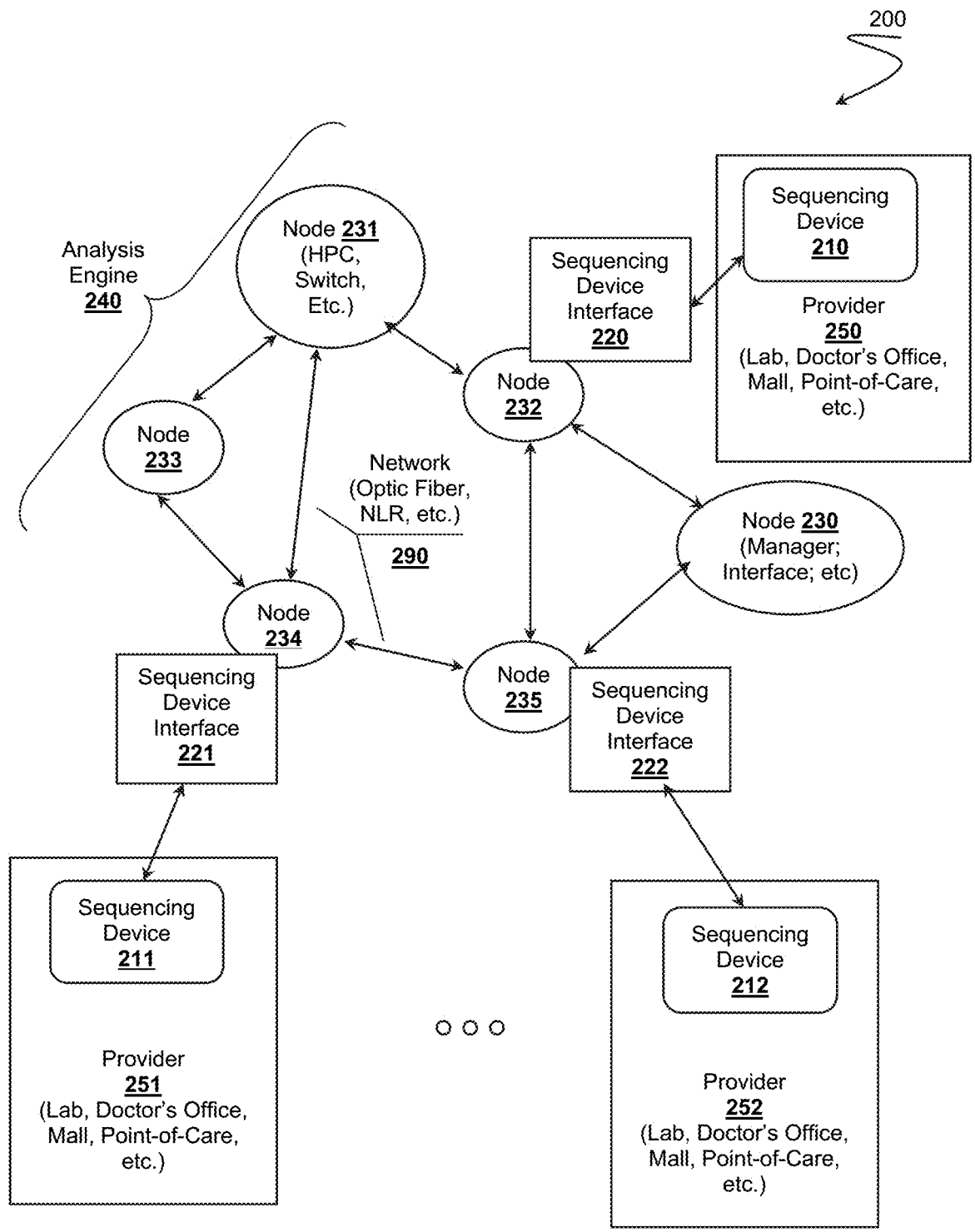
FIG. 2 is a schematic of a genomic analysis engine capable of interfacing with sequencing devices via one or more sequencing devices.

FIG. 2 presents an overview of a genomic analysis system 200.

Analysis engine 240 can be distributed across many nodes (e.g., nodes 230, 231, 232, 233, 234, and 235 are illustrative of the kind and number of nodes, which are not limited to those depicted in FIG. 2) interconnected by a network such as the NLR 290, an optical fiber network, an integrated or standalone wide area network, metropolitan area networks, enterprise private network, virtual private network, intranet, wireless network, or other networks.

Nodes 230, 231, 232, 233, 234, or 235 can include computers, clients, servers, peers, or preferably includes High Performance Computing facilities (HPCs) 231. Nodes can also include network infrastructure itself, switches (e.g. Cisco®, Juniper®, etc.), modems, repeaters, hubs, bridges, application layer gateways, routers, multilayer switches, converters, host bus adapters, hubs, firewalls, or other network elements. One should appreciate that nodes 230, 231, 232, 233, 234, or 235 can be considered to be fungible with respect to conducting genomic analysis where each node can comprise one or more genomic analysis modules capable of analyzing sequence data.

Nodes 230, 231, 232, 233, 234, or 235 can be general genomic analysis nodes, general purpose nodes configured or programmed for genomic analysis, nodes dedicated to a specific genomic analysis role or responsibility such as routing, processing, sequencing, forwarding, data-cleansing, mapping, or other functions. Regardless of a specific node's roles or responsibilities, in some embodiments the roles or responsibilities can migrate from node-to-node should a loss of node require shifting the lost node's functionality to another node.

Nodes 230, 231, 232, 233, 234, or 235 can include analysis management nodes 230 governing a specific analysis such as DNA and RNA sequence analysis, gene expression profiling, alignment analysis, genome comparison analysis, pattern searching, DNA motif analysis, DNA promoter analysis, DNA and/or RNA secondary and tertiary structure analysis, DNA copy number variation, DNA methylation, microRNA analysis, mRNA expression profiling, splice variant analysis, protein sequence (and in some cases, structural) analysis, or other genomic analysis tools and methods (e.g., phylogenetic tree assembly, calculation of evolutionary distance, determination of mutation rate, etc.).

One acceptable form of node can include one or more modeling engines operating on Graphics Processor Units (GPUs) as described in co-owned U.S. provisional application having Ser. No. 61/673,943, filed Jul. 20, 2012, herein incorporated in its entirety by reference and to which this application claims priority.

Nodes 230, 231, 232, 233, 234, or 235 can include analysis facility management capabilities governing portions of the system or all of the genomic analysis system. There can be a manager node 230 operating as an interface to the system with automatic or user-generated dashboards to monitor or manage the genomic data stream, or genomic analysis flow. The manager node 230 may be used to create annotations or notations on the data, create processing instructions, normalize data or analysis, manage memory, or other functions. The manager node 230 can define constants, naming conventions, properties, navigation methods, manipulator methods, utility methods, data and analysis quality control parameters, and other functions. One should appreciate that manager node 230 can offer an interface through which a user (e.g., a system manager, administrator, end-users, etc.) can use to make requests for functions or analysis. The manager node 230 can be configured or programmed through an API, a client computer or server, laptop, tablet, mobile device, browser, or other interfaces. The manager node 230 can be used to add, repeat, alter, or cancel analyses; ascertain or set properties of the sequenced data; merge or align sequenced data with data found in genome database repositories; re-route analyses; or other functions.

Nodes 230, 231, 232, 233, 234, or 235 can operate alone or in aggregate according to the desired analyses. The nodes 230, 231, 232, 233, 234, or 235 can operate in series, in parallel, iteratively, or some combination thereof. Such an approach is considered advantageous because the nodes allow for arranging the nodes into specific configurations or topologies that address general purpose processing or customized processing of genomic data. For example, nodes 230 through 235 could be configured into a patient specific topology where each of the nodes operate on different portions of the patient sequence data, or where each node applies a different analysis regime to the sequence data. Such an approach is considered advantageous when specific analysis or urgency is required for a patient, or where particular analysis of data requires substantial processing time/resources.

The analysis engine 240 is comprised of nodes 230, 231, 232, 233, 234, or 235 and the network 290, possibly operating under the governance of manager node 230. The analysis engine 240 obtains genetic data from sequencing devices 210, 211, or 212 (sequencing devices 210, 211, and 212 are illustrative of the kind and number of sequencing devices, which are not limited to those depicted in FIG. 2). The sequencing devices 210, 211, or 212 can be configured or programmed to communicate with the analysis engine 240 (e.g., engine 240 as a whole, individual nodes 230-235, via manager node 230, etc.). The sequencing devices 210, 211, or 212 can communicate with the analysis engine 240 via sequencing device interfaces 220, 221, or 222 or other internet, network, or communications protocols and interfaces. Example interfaces can leverage one or more protocols possibly including one or more of Transmission Control Protocol (TCP), Hypertext Transfer Protocol (HTTP), Common Internet File System (CIFS), Network File System (NFS), File Transfer Protocol (FTP), Secure File Transfer Protocol (SFTP), Hypertext Transfer Protocol Secure (HTTPS), Network Address Translation (NAT), Secure Copy Protocol (SCP), or others protocols known or yet to be implemented. For example, sequencing devices 210 through 212 can be configured to operate behind one or more firewalls. Upon deployment in their corresponding provider's offices, sequencing device 210 through 212 can send an HTTP request through the firewall to one or more of device interfaces 220 through 222, which can be configured as an HTTP server. Upon reception of the request, the device interfaces 220 through 222 can establish a connection (e.g., a TCP/IP session, SSL session, etc.) with corresponding sequence devices, possibly via a NAT connection through the firewalls. Sequencing device 210 through 212 can then send their genomic data to nodes 230 through 235 via interfaces 220 through 222 perhaps as a raw data stream, as files via FTP, as an XML stream, or other format.

As example, an initial experiment of analysis stream management utilized a proprietary UDP-based client-server architecture dubbed "Transporter" where data streams are encrypted for provided using AES-128. The initial implementation includes 20 instances of Transporter clients, each were run in Sunnyvale, Calif., each with two threads, a Maximum Transmission Unit (MTU) of 9000 and a rate limit of 240 Mb/sec/thread. All Transporter client instances simultaneously connected to three instances of the Transporter server running in Phoenix, Ariz. All transfer and processing statistics were collected using the Zabbix monitoring package. The median transfer speed was 8.232 Gb/sec, as measured at the firewall in Phoenix, with the top 1% of traffic reaching peak transfer rates of greater than 9.55 Gb/sec. This overall transfer speed represents a throughput of one exome every 17.4 seconds. In the experimental setup, the stream object represented the flow of data from one end point to another (e.g., threads and instances of Transporter) for each patient as well as the analysis and transport of the data. Further, the stream object can be considered to also represent the collected or monitored statistics.

Sequencing devices 210, 211, or 212 are typically located at remote facilities or healthcare providers 250, 251, or 252 such as at point of care, a mall, doctor's office, pharmacy, research or clinical lab, or other locations. Sequencing devices 210, 211, or 212 determine the sequence of nucleotides in a biological sample. Legacy sequencing devices lacking a capability to interface with contemplated analysis system 200 can be configured to interface to the analysis engine 240 via a sequencing device interface 220, 221, or 222. The sequencing device interfaces can be constructed as aftermarket modules that configure or otherwise adapt the sequencing devices to couple with analysis engine 240. Example technologies that could be configured as a genomic device interface could include device servers products offered by Digi International, Inc. (see URL www(dot)digi(dot)com; Digi Connect ME, Digi Connect Wi-ME, PortServer, etc.) or Lantronix Inc. (see URL www(dot)lantronix(dot)com;) XPort®, xPico™, UDS1100, WiPort®, etc.). Such a device server can be instrumented with genomic analysis modules to operate as sequencing device interfaces 220 through 222 or could be integrated into sequencing devices 210 through 212.

Sequencing devices 210, 211, or 212 could be located at point of care, a mall, doctor's office, pharmacy, lab, or other provider locations 250, 251, or 252. As sequencing devices 210, 211, 212 become more prevalent and cost effective, they can be located anywhere. The sequencing devices 210, 211, or 212 may be accessible on mobile hand-held devices, security devices that can be used by the Transportation Security Administration (TSA), portable devices, in laboratories, laptops, or other devices. The sequencing devices 210, 211, or 212 can be delivered to emergency areas that may urgently need to ascertain the nature of a disease outbreak identified by the Centers for Disease Control and Prevention (CDC) or similar public health agency, to track an emerging epidemic in developing or developed countries, or to address biological threat in a terrorist, wartime, or conflict situation.

The network itself 290 or the providers 250, 251, or 252 can have a report server (e.g. Microsoft Reporting Services Report Server) or other reporting engine (not depicted in FIG. 2) to provide reporting templates, user-defined reports, genome drawing tool, visual output, or other information. There can be report builders, report designers, or other ways to generate reports.

Sequencing device interfaces 220, 221, or 222 can operate as "adaptors" to connect the sequencing device to the "cloud" represented by analysis engine 240. The sequencing device interfaces 220, 221, or 222 can be local to the sequencing device if it is a legacy device (not depicted) lacking desired communication capabilities, passive, or has no knowledge of other devices to which it is connected. A single sequencing device interface 220, 221, or 222 could connect with one or more other devices to exchange data according to an analysis requirement. Sequencing device interfaces 220, 221, or 222 might be managed according to maker, model, affiliations, medical group, or other classification. Thus, manager node 230 can communicate with the sequencing devices to ensure each device properly operates within the ecosystem or participates according to a desired analysis.

The entire system 200 is preferably constructed to operate in parallel. The genomic analysis system 200 can support the processing of hundreds, thousands, or more sequencing devices at the same time, and the system 200 can analyze hundreds, thousands, or more patients at the same time. The system 200 can also support the processing or genetic analysis of populations or groups of samples.

The genomic analysis system 200 is capable of processing many patients in parallel at a high rate. The processing rate can be based on how many patients per unit time are being processed at a given time, possibly processed to completion. For example, the genomic analysis system 200 can be configured to process sequence data into genome data at a rate of at least five patients per day. In exemplary embodiments, the genomic analysis system 200 can process sequence data into genome data at a rate of at least ten patients in one day, more preferably at least ten patients in one hour, yet more preferably at least one hundred patients in one day, or even more preferably at least one hundred patients in one hour.

The analysis engine 240 processes genomic data. The analysis engine 240 can process genomic data from a patient individually, and the analysis engine 240 can compare genomic data from a patient against a population dataset or sample with similar demographics or other grouping. The Applicant coins the term "Homo Statisticus" to represent a statistical or baseline genome data of a human against which patient data can be compared. Homo Statisticus representations can include data found in public genome databases, evolving databases that continuously collect data, private databases, or a normalized sequence. The analysis engine 240 can process the sequence data to generate genome data as a function of a normalized genomic sequence. The normalized gene sequence can be a statistical compilation from a population or sub-population of patients or other data sources. Based on the normalized genomic sequence, the genome data can comprise a hot spot, a weighted reference point, or a prioritization for analysis. The analysis engine 240 can also produce a differential sequence or a rough alignment based on the normalized sequence.

The analysis engine 240 can provide feedback to sequencing devices 210, 211, or 212. The analysis engine 240 can utilize management node 230 as an interface and configured or programmed to allow the user to provide feedback between sequencing devices 210, 211, or 212. The user can provide sequencing device instructions such as requests to repeat sequencing, to start or stop sequencing, to send or receive data, to delete data, to manage licensing, or other instructions.

A genomic analysis stream can be considered a stream of data from sequencing devices 210, 211, or 212 through the analysis engine 240 to a point of notification such as providers 250, 251, or 252. Thus, an analysis stream can be considered a distinct manageable object which can be controlled, manipulated, or otherwise managed. Stream objects can include stream attributes that describe the nature of the stream. Example attributes include a stream identifier (e.g., GUID, UUID, name, etc.), an analysis topology, point of origin information (e.g., point of care identifier, sequencing device identifier), point of notification information (e.g., healthcare provider identifier, etc.), patient information, notification trigger criteria, billing codes, billing or invoicing information, or other information related to the stream. Manager node 230, or other elements within the system, leverage the stream attributes to properly manage the stream with respect to analysis, routing, reporting, alerting, or other management functions. Stream objects can further include the genomic data actually being processed at the various stages of analysis. One should appreciate that stream object is also considered to represent the data flow of the genomic data. Thus, stream of data can be processed in batches at the same time or can be managed as a full stream from end-to-end. The genomic analysis can be conducted simultaneously as the data or results are collected and delivered to a user. The stream can be a manageable object managed by manager nodes 230. The manager nodes 230 are able to manage the analysis engine 240 by managing at least one analysis stream object (e.g., an analysis data stream, an analysis route applied to sequence data etc.) according to one or more management functionalities possibly including modifying an analysis route, instantiating an analysis stream according to the stream object, conducting a transaction based on the analysis stream object, altering an analysis, constructing a notification trigger criteria based on the analysis stream object, deconstructing an analysis stream, or other management functionality to manage the analysis stream.

The analysis engine 240 is considered a dynamic system that can change its processing, analytical, or routing configurations as needed for genomic analysis. The manager node 230 can be controlled by a user or can be configured to manage and configure other nodes in an analysis operation automatically. These configuration changes or instructions manage the analysis stream, and they can include stream management functionality such as generating a notification as a function of genome data, a processing status, an analysis engine management status, an alert, an alarm, a sequencing device instruction, an analysis recommendation, a prognosis, a diagnosis, an inter-node communication, a request to obtain a higher confidence level, or other notifications. The manager node can also generate a notification that configures a route within the analysis network. Not only can the manager node reroute streams but it can also process chains of nodes to manage the overall analysis stream.

Management node 230 offers one or more tools to manage the analysis nodes 230, 231, 232, 233, 234, or 235, the analysis stream, and the analysis engine 240. The management node 230 can include a dashboard to manage the entire system, a dashboard for a particular group, a dashboard for subscribers, a dashboard for signal analysis, user-defined dashboards, a dashboard to design reports and outputs of the analysis, a dashboard for input and output analysis, a visual dashboard to monitor the system, or other dashboards. One should appreciate that contemplated dashboards can present information with respect to genomic analysis stream objects where an overview can be presented indicate how a collective of stream objects are being processed, possibly viewed in real-time. Further, stream objects can be controlled via such dashboard by instantiating streams, deconstructing streams, deactivating streams, monitoring system efficiency with respect to streams, or applying other controls.

The analysis system 200 can be configured or programmed to route data or analysis streams. The analysis engine 240 can be configured to establish processing routes among the analysis nodes 230, 231, 232, 233, 234, or 235, depending on the state of sequenced data, how other genomic data is routed, and how loaded the analysis system is. The analysis engine 240 can establish processing routes as a function of expected diagnosis, prognosis, priority, urgency, sequence annotations, traffic load, analysis load, computation bandwidth, memory constraint, alert status, status of analyses, user-defined inputs, type of genomic analysis, number of analysis iterations required or requested, confidence level, or other analysis parameters. In such embodiments, analysis engine 240 can take on a specific configuration that suits a current analysis. For example, prioritized data can be routed to a high volume processing node while less urgent data can be run as a batch processing on a low volume node. Consider a scenario where patients are associated with a particular demographic having a low probability of exhibiting an undesirable mutation. Manager node 230 can configure one or more other nodes according to a high volume, high throughput topology based on the demographic information or genomic profile information. The high volume, high throughput topology processes corresponding patient data as it comes in, possibly forming one or more FIFO buffers of streams. When a particularly interesting patient data stream is introduced, perhaps due to urgency or an emergency, manager node 230 allocate one or more nodes as a dedicated topology to analyze the urgent patient's data. Acquisition of such resources could impact the high volume, high throughput topology. However, the urgent patient's data can be processed in a timely fashion to address the urgency or emergency.

The analysis engine 240 can operate as a for-fee service, which requires subscribers to register, submit payment information, or log into the system in order to access the genomic analysis capabilities. The nodes 230, 231, 232, 233, 234, or 235 such as the management node 230 can manage the subscriber list, licensing requirements, login functionality, payment system, and other for-fee related functions. As genomic analysis stream objects are processed by analysis engines 240, one or more of manager node 230 can monitor the extent of resources or services are applied to analysis. Based on a calculated use, the manager node 230 can charge a fee to one or more accounts (e.g., healthcare provider account, insurance account, patient account, etc.) in exchange for supplying the rendered services. One should appreciate that fees can be applied based on among of resources required for analysis, urgency, prioritization, algorithms used for analysis, or other genomic analysis stream object attributes.

The analysis engine 240 can be further configured to process sequence data based on image recognition. The sequencing devices 210, 211, or 212 can also be configured to process sequence data based on image recognition. It is contemplated that genome output or other data output from serial time-encoded amplified microscopy (STEAM) or other process can be translated to a DNA base. At the base calling step, each image from a data output can operate as an indicator for a particular DNA base. For example, the images can be considered a form of a barcode, which can be recognized. Further, the images can be part of the analysis stream transported through the analysis system.

STEAM is a method of high-throughput imaging. Unlike conventional image sensors like charge-coupled devices (CCDs) and complementary metal-oxide-semiconductor (CMOS) devices, STEAM can provide extremely fast shutter speeds without high-intensity illumination. The STEAM method maps a two-dimensional image into a one-dimensional amplified serial time-domain waveform. STEAM achieves this by first stamping information onto the spectrum of a broadband optical pulse and then mapping the spectrum into a time-domain serial stream. This method is configured to provide both image streaming and amplification and is configured to capture rapid physical phenomena under high speeds. STEAM has frame rates that are at least 1,000 faster than conventional CCDs and as high as 6.1 million frames per second, Moreover, this method offers a shutter speed of 27 ps (picoseconds).

As a method of high-throughput imaging, STEAM can be used to identify rare diseased cells, cancer cells, or other biological or genomic material. This cell identification method can have numerous applications in the analysis system 200 including cancer screening and other diagnostic tests.

It is further contemplated that the analysis system 200 may use an algorithm such as scale-invariant feature transform (SIFT) or other algorithm to perform the image recognition. SIFT is a widely known algorithm for image recognition which uses a class of local image feature vectors that are invariant to illumination, image noise, scaling, translation, viewpoint, transformations, and rotation. Features are detected through staged filtering (i.e. scale-space extrema detection, keypoint localization, orientation assignment, generation of keypoint descriptors, etc.), and image keys are created for them. Thus, images obtained from the analysis system can be analyzed to determine if they have image features (e.g., SIFT features, etc.) that correspond to features related to known objects.

Example techniques that can be used for conducting genomic analysis include those offered by Five3 Genomics, LLC (see URL five3genomics(dot)com) as discussed in U.S. patent application publications 2012/0066001, and in international patent application publication WO 2013/086424, WO 2013/086355, WO 2013/062505, WO 2013/052937, and WO 2011/139345. Additional techniques include time-encoded amplified microscopy (STEAM), and techniques discussed in 2012/0059670 to Sanborn et al.

Genomic Analysis Stream Management via Add-on Modules

Figure 3:
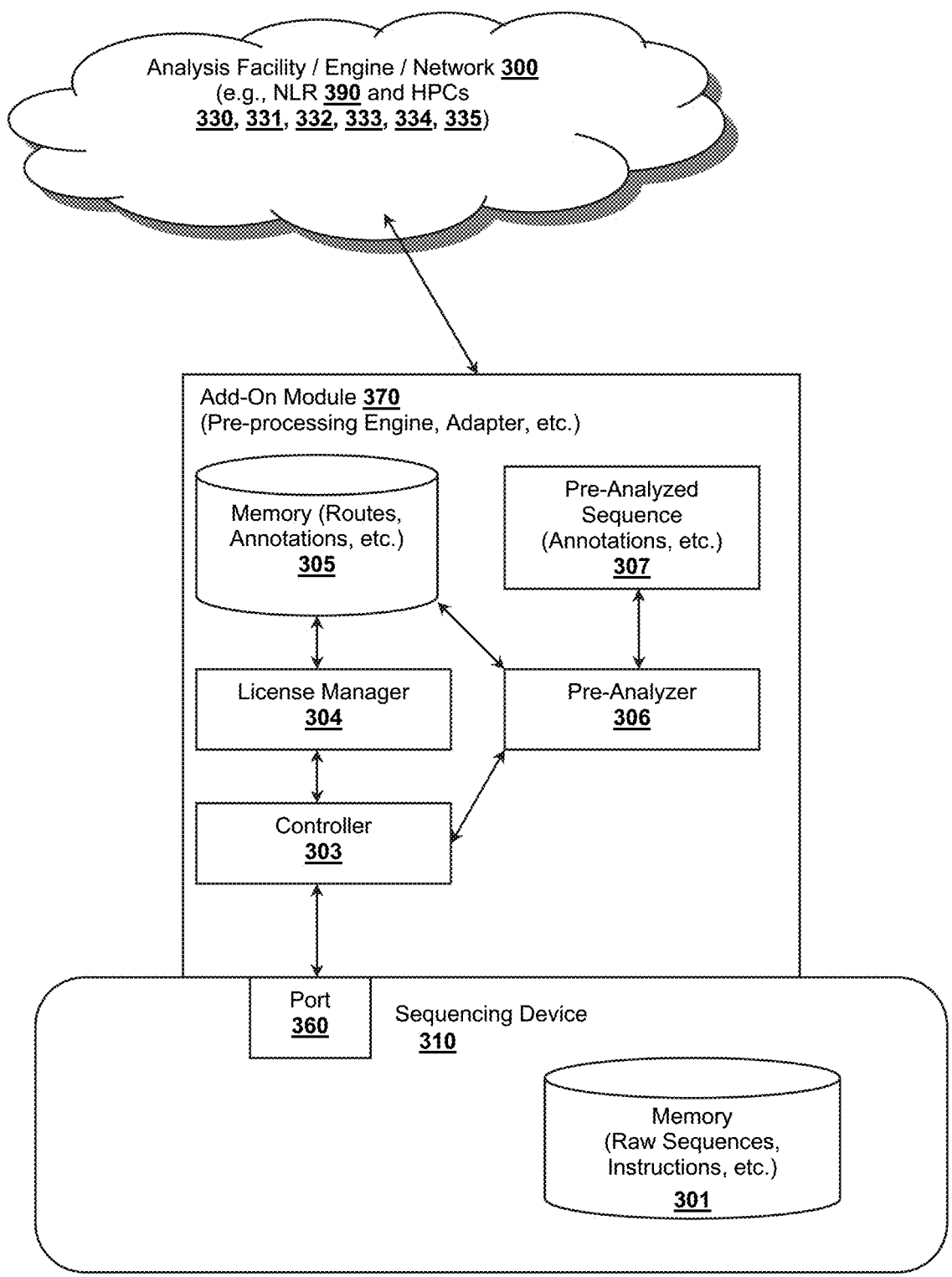
FIG. 3 is a schematic of an add-on module capable of configuring a sequencing device to interact with a genomic analysis facility.

FIG. 3 illustrates another aspect of the inventive subject matter where an add-on module 370 can be used to configure a sequencing device 310.

The add-on module 370 can be an after-market device, or the add-on module 370 can be integrated into the sequencing device 310 itself Alternatively, the add-on module 370 can be integrated into the analysis cloud 300 (e.g., a web service, software as a service (SaaS), infrastructure as a service (IaaS), platform as a service (PaaS), etc.) or other configuration. The add-on module 370 can also comprise an application package or cloud-based application executing on one or more hardware platforms.

The add-on module 370 can be configured or incorporated in a variety of ways to facilitate communication between devices, analysis streams, or analyses among and between the analysis system 300 (e.g. NLR 390 and HPCs 330, 331, 332, 333, 334, or 335). The add-on module 370 can be configured to package the pre-analyzed sequence data according to many transfer formats, where the transfer format can be defined by each analysis facility/node 330, 331, 332, 333, 334, or 335. The add-on module 370 can be a hardware module configured to couple with a legacy sequence device 310 operating as a sequence device, to couple with legacy devices 310 within existing sequencing devices, or to couple legacy devices with other devices. The sequencing device 310 itself can operate as the add-on module 370. The sequencing device 310 can also include storage medium 301 for storing instructions comprising the functionality of the add-on module 370. The add-on module 370 or its functionality can be integrated in analysis nodes 330, 331, 332, 333, 334, or 335, or the add-on module 370 can operate as a software adapter that communicates with a remote network-enabled sequencer 310. Other configurations of the add-on module 370, sequencing device 310, and other devices are contemplated, whether as integrated devices, nested devices, devices with integrated functionality, or segregated devices or functionality.

The add-on module 370 preferably conducts pre-processing to annotate raw data for further analysis. The sequence annotations of the raw data aid the analysis system 300 in describing how data should be analyzed. The sequence annotations can incorporate many kinds of annotations such as the ownership of the analysis node, ownership of the data, the raw input data, the pre-analyzed and annotated sequence, the outputs; the routing of the analysis and the data streams; and other factors. The sequence annotations can provide a rough alignment between the raw data and pre-existing or public genome databases to get a preliminary diagnosis, prognosis, or other analysis result. For example, sequence annotations may include patient-specific data, disease or diagnosis-relevant or related data, data identifying putative or actual sequence location in the genome, etc. Thus, the sequence annotations can also provide more extensive preliminary analysis such as annotating how the raw data fits within a larger analysis, the priority information (e.g. which genes or hotspots should be analyzed first and where), urgency information, or other factors. For example, add-on module 370 can receive sequence data from sequencing device 310 and pre-analyze the sequence data. Pre-analyzer 306 could package the sequence data within an XML file stream and include annotations indicate various rules, requirements, or other factor as tags within the XML file stream.

The add-on module 370 can communicate with the analysis system 300, the analysis engine 240, the sequencing device 310, or the analysis nodes 330, 331, 332, 333, 334, or 335 via one or more wired or wireless connections as desired. The add-on module 370 can utilize all forms of wired or wireless connections to connect to the analysis engine 240 and analysis nodes/facilities 330, 331, 332, 333, 334, or 335, including cellular connections (e.g., GSM, CDMA, etc.) WiMAX, WiGIG, Wi-Fi, Wi-Fi Direct, or other type wireless infrastructure. The add-on module 370 can also use all forms of wired or wireless connections to connect to the sequencing machine 310 such as the Ethernet, WiFi, WiGIG, USB, W-USB, Bluetooth, or all other forms of connectivity.

Add-on modules 370 can comprise a number of additional components that allow the modules to interact with the analysis facility 300 or with a sequencing device 310. Example components include licensing manager 304, controller 303, memory 305, and pre-analyzer 306. As raw data is obtained from sequencing device 310, pre-analyzer 306 can pre-process the data to form one or more pre-analyzed sequence 307.

The controller 303 couples with the sequencing device 310. Alternatively, the controller 303 can couple with the sequencing device 310 through a port 360. The controller 303 provides a bi-directional data path through which commands, instructions, raw data, annotations, analysis streams, and other information can be exchanged between the sequencing device 310, the add-on module 370, and the analysis system 300. The controller 303 can further receive commands from the analysis system 300 and analysis facilities/nodes 330, 331, 332, 333, 334, or 335 to control the sequencing device 310.

The add-on module 370 can also include a pre-analyzer 306 that obtains raw data (i.e., data received directly from sequencing device 310) and conducts pre-analysis to yield pre-analyzed sequences 307. Pre-analysis can generate sequence annotation based on sequence or other genomic data in the memory 301 of the sequencing device 310, the memory of the add-on module 305, the memory from the distributed analysis network 300, analysis facilities/nodes 330, 331, 332, 333, 334, or 335, public data sources, or other data sources. The add-on module 370 generates pre-analyzed sequences 307, which can include sequence annotations along with other data derived from the raw sequence such as preliminary gene identifications (e.g., by name or function), genomic hotspots, genomic comparisons (e.g., to reference sequence, or prior test), patient vs. population comparisons, rough alignments comparing the raw data with sequenced genome data from public genome databases or other databases, and other data. Other annotations may also include putative location, disease association, relative abundance information, gene association, class of nucleic acid, chain of custody, origin of tissue or tissue sample, patient information, patient identifier, demographic information, geographic information, diagnostic information, healthcare provider information, intent of sequence analysis, account information, familial information, patient history, psychographic information, germ line, or others.

The add-on module 370 allows the sequencing device 310 to communicate with the analysis system 300 and analysis facility/nodes 330, 331, 332, 333, 334, or 335. The add-on module 370 forwards the pre-analyzed data 307 to the analysis facility/nodes 330, 331, 332, 333, 334, or 335 for further processing and can forward the pre-analyzed data 307 to the facility/nodes 330, 331, 332, 333, 334, or 335 based on sequence annotations 307. For example, the add-on module 370 might forward routine or urgent data to the Centers for Disease Control and Prevention (CDC), research facilities, or other facilities 330, 331, 332, 333, 334, or 335.

The add-on module 370 can also generate sequence annotations 307 that control the processing of the data within the same sequencing device 310 or the processing of data at other analysis nodes/facilities 330, 331, 332, 333, 334, or 335. These annotations create processing parameters such as routing parameters, analysis parameters, path parameters, destination parameters, source parameters, priority parameters, urgency parameters, class of service parameters, billing parameters, payment parameters, license control parameters, administrative processing parameters, or other processing parameters.

License manager 304 allows module 370 to control operational access to the analysis facility or nodes 330, 331, 332, 333, 334, or 335 accessible through the analysis system 300. The license manager 304 can include one or more keys (e.g., subscription keys) as well as incorporate different information or methods of authorization or authentication such as having a subscription identifier, a number of permitted uses, a licensing term, a permission level for types of services or types of analyses, indicators for allowable types of services or analyses, an analysis account, and an analysis management module.

License manager 304 can operate as a rights management enforcement module. In some embodiments, license manager 304 is configured or programmed to, according to a licensing rules set, consult analysis engine 300 to determine if sequencing device 310 has sufficient rights or privileges to access services offered by analysis engine 300. For example, sequencing device 310 might be deployed within a physician's office. The physician could pay a subscription fee to access one or more services of genomic analysis engine 300. License manager 304 can consult the physician's subscription account to determine if the physician is in good standing, or determine a level of service to which the physician has access. As sequencing device 310 supplies data to analysis engine 300, license manager 304 can properly account for the physician's interactions with analysis engine 300.

One should appreciate that license manager 305 can also monitor or otherwise manage one or more genomic analysis stream objects related to sequencing device 310 with respect to an account. The account could include a point of care provider's account, a patient's account, an insurance account, or other accounts. As sequence data is generated via sequence device 310, license manager 304 can attach a stream object identifier to the sequence data as an annotation that allows the analysis engine 300 to properly route or otherwise direct analysis.

Genomic Analysis Stream Pre-Processing of Sequence Data

Figure 4:
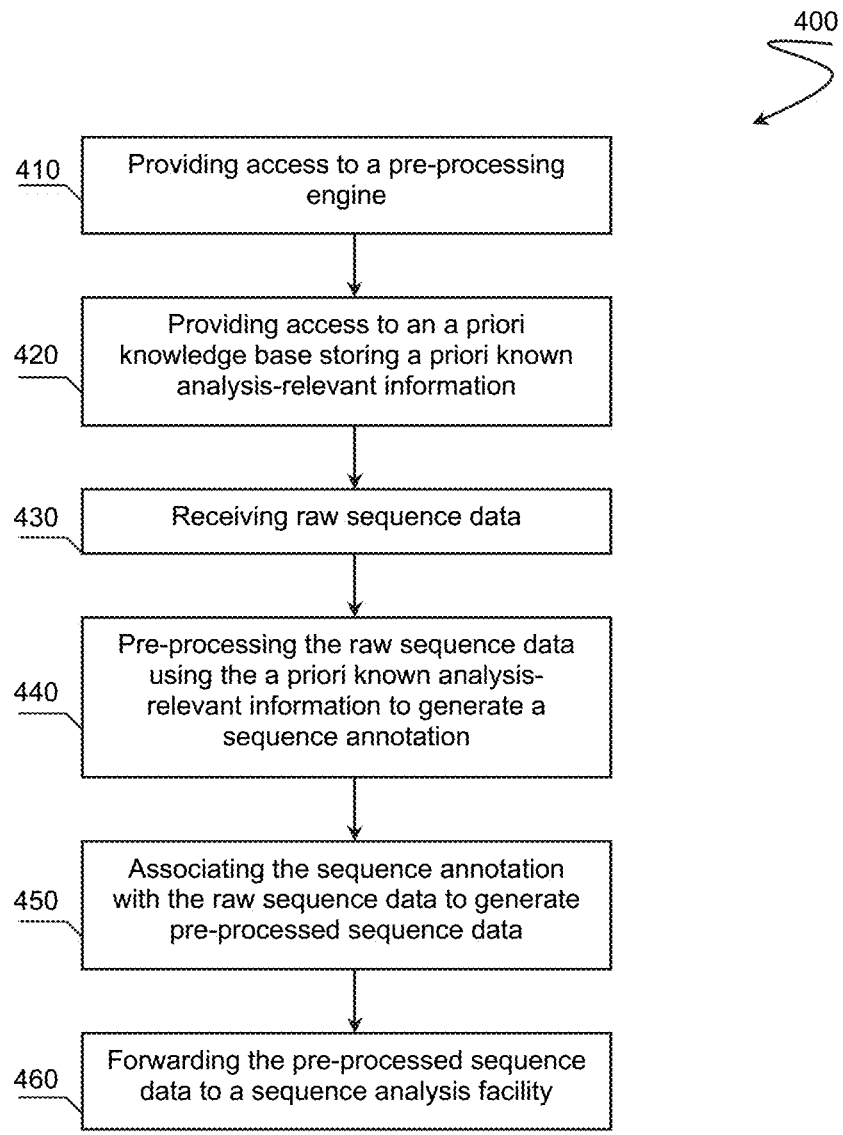
FIG. 4 is a schematic of a method for pre-analyzing genomic sequence data.

FIG. 4 illustrates a method 400 for pre-processing genomic data that could be used in conjunction with the add-on module 370 of FIG. 3 where add-on module 370 from FIG. 3 could operate as a pre-processing engine.

Method 400 can begin at step 410, which can include providing access to a pre-processing engine. For example, the pre-processing engine could include one or more of add-on modules 370 discussed with reference to FIG. 3. Step 410 may also require users to subscribe to a service or license, unlock access, install software, authenticate their access, authorize their access, or utilize other forms of authentication to access the pre-processing engine. One should appreciate that providing access can cover a broad spectrum of actions including selling pre-processing engines, installing pre-processing engine, incorporating pre-processing engines into a legacy device design, or otherwise making a pre-processing engine available.

Step 420 can include providing access to an a priori knowledge base storing known analysis-relevant information. The knowledge base may include analysis-relevant data about known sequences or other forms of analysis data. The knowledge base may be located at analysis facilities 300 as shown in FIG. 3, public genomic databases, laboratory databases, proprietary databases, user-defined or created databases, or other knowledge bases. The data is used by the pre-processing engine to properly annotate sequence data for further analysis. The knowledge base can be in the memory 305 of the add-on modules 370 as shown in FIG. 3, can be available in the memory of remote locations, can be in the memory 301 of the sequence machine 310 as shown in FIG. 3, can be a database to which one subscribes, or can be any kind or form of memory.

At step 430, the pre-processing engine receives the raw sequence data, typically directly from a sequencing device 310 as shown in FIG. 3. The raw sequence data can be from a memory, buffer, database, or other sources. The raw data sequence data could be of any format (e.g. Axt, BAM, BAMBAM, BED, MAF, microarray, SAM, WIG, XML, or other format). The raw sequence data can comprises data received from a sequencing device that is to be pre-processed before complete analysis.

The method of pre-processing 400 can also include step 440 of performing a rough alignment of the raw data against a known genomic map from any a priori knowledge base to generate a sequence annotation. The rough alignment of the raw data facilitates the processing and analysis of genomic data by roughly aligning the raw data based on a position relative to a chromosome, a position relative within a chromosome, association with a known allele, association with a known marker, association with a known mutation, or association with any known pattern or sequence from an a priori knowledge base or collection of empirical data.

The pre-processing of raw data can occur in parallel with analysis occurring throughout the analysis system 300 as shown in FIG. 3. A part of the data stream that has already been pre-analyzed can be forwarded for analysis through the analysis system 300 as shown in FIG. 3 while newer sections of the data stream are being pre-processed. This parallel processing can be done in real-time based on sequencer output.

Step 450 can include associating the sequence annotation with the raw sequence to generate pre-processed sequence data. This step includes pre-processing to determine some level of content of the raw sequence data. Associating sequence annotations with the raw sequence can be based on one or more policies or rules according to information from the knowledge base in order to annotate the raw sequence data properly.

The sequence annotations can cover a broad spectrum of information. The sequence annotations can comprise a position in a genome (e.g., on specific chromosome or chromatid, extrachromosomal, etc.), a known disease marker, a mutation (e.g., point mutation/transition/transversion, insertion, deletion, translocation, etc.), a diagnostic code, a procedural code, a billing code, analysis routing information, statistical information, patient information, a demographic, a geographic coordinate, a chain of custody, and others. The sequence annotations can also comprise a recommendation to the healthcare provider, a treatment recommendation, a recommendation for preventative or curative treatment, a suspected diagnosis, an estimated prognosis, an analysis prioritization, an alert trigger, an alert notification, a request for further analysis, a request for a higher level of confidence, a list of possible outcomes, a required or voluntary course of treatment, an indication of risk or predisposition to a particular condition, or other information.

Step 460 can include forwarding the pre-processed sequence data to a sequence analysis facility for further or more detailed analysis. The process of forwarding the pre-processed sequence can include transmission of the annotated pre-processed sequence data to an analysis facility 330, 331, 332, 333, 334, or 335 as shown in FIG. 3. These pre-processed sequences are preferably pushed to the facility 330, 331, 332, 333, 334, or 335 as shown in FIG. 3, but the pre-processed sequences could also be pulled by the facility 330, 331, 332, 333, 334, or 335 as shown in FIG. 3. The transmission of the pre-processed sequences can be via suitable protocols such as HTTP, FTP, SSL, HTTPS, proprietary, XML, or others.

Interactive Genomic Analysis Stream Management Systems

Figure 5:
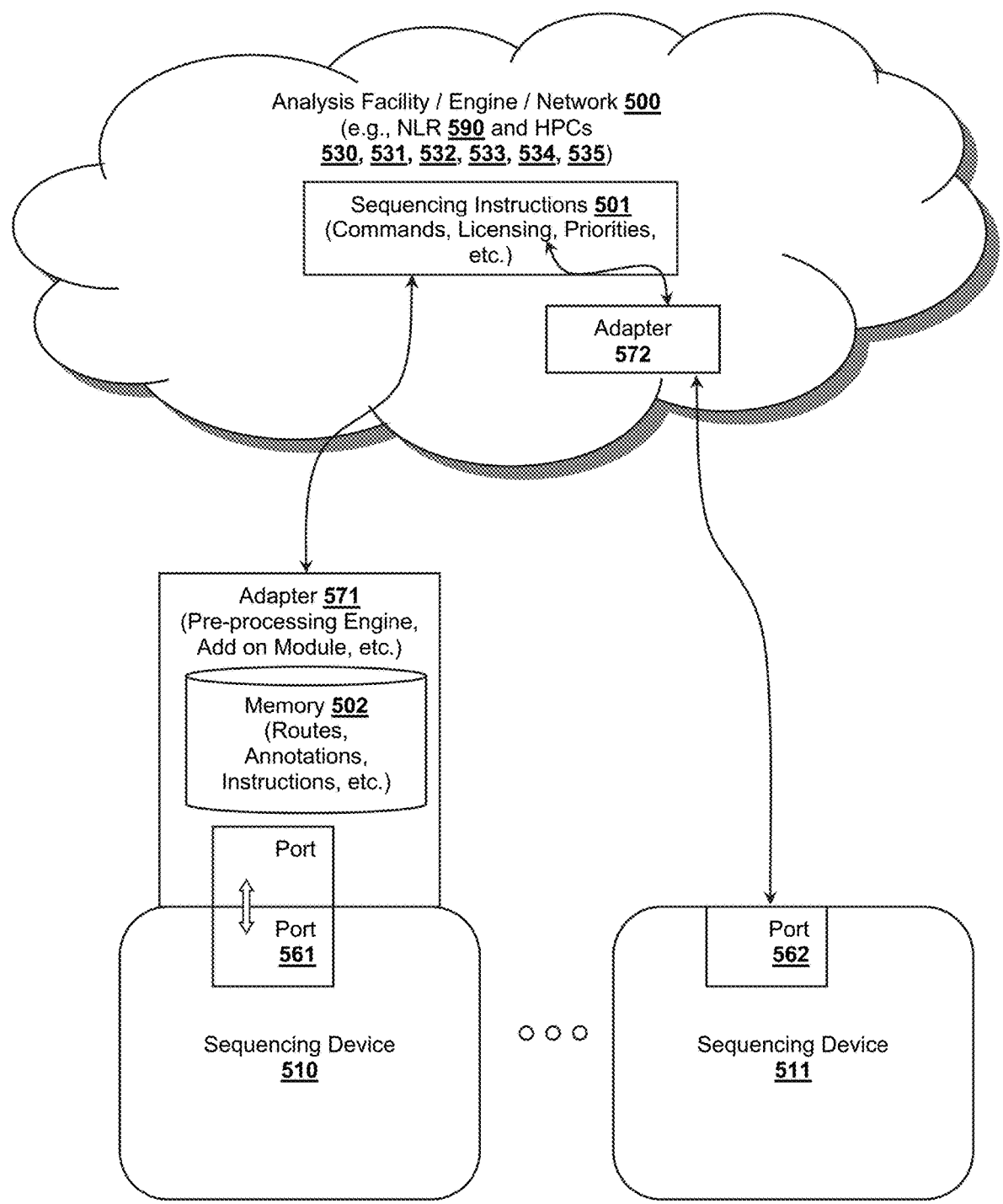
FIG. 5 is a schematic of an interactive sequencing system where an analysis facility can provide sequencing instructions to a sequencing device.

FIG. 5 illustrates yet another aspect of the inventive subject matter where an analysis facility 500 is capable of interacting with one or more sequencing devices (e.g. sequencing devices 510 or 511). The facility 500 is able to access or control the sequencing devices via an adapter 571 or adapter 572. As mentioned previously, the add-on module 370 in FIG. 3 is a suitable candidate for an adapter. Although adapter 571 and adapter 572 are illustrated as external to sequencing devices 510 and 511, respectively, it is also contemplated that the roles or responsibilities of the adapters could be integrated or incorporated into future versions of sequencing devices 510 through 511.

The contemplated analysis system in FIG. 5 includes an analysis engine (e.g. NLR 590 and HPCs 530, 531, 532, 533, 534, or 535) and an adapter 571 or 72. As discussed earlier, the adapter 571 and 572, or add-on module 300 as shown in FIG. 3 can be a device attached to the sequencing device 510, can be integrated within the sequencing device 510 or 511, is the sequencing device 511 itself, or can be available or operating as an adapter 572 as part of an analysis cloud possibly 500 built on the NLR 590 and the analysis nodes 530, 531, 532, 533, 534, or 535. In other embodiments, the adapter 571 and 572 can communicate with sequencing devices 510 or 511 through ports 561 or 562. One should appreciate that adapters 571 or 572 can take on different forms depending on the target sequencing device as illustrated.

The analysis engine 500 can conduct a partial or a full analysis of a genomic sequence via the analysis system in FIG. 5.

The adapter 571 couples with a sequencing device 510 and allows for bi-directional communication between the device 510 and the analysis facility 530, 531, 532, 533, 534, or 535 or even among other elements in the ecosystem 500. The adapter 571 could allow multiple sequencing devices to operate in parallel in a coordinated fashion.

The adapter 571 or 572 can also allow the facility to submit commands or instructions 501 to the sequencing machine 510 or 511. In some embodiments, the adapter 571 or 572 converts the instructions 501 from a "facility" format to a command understandable by the sequencing device 510 or 511.

The adapter 571 can be located proximate to the sequencing device 510, or distal in the case of adapter 572 distal from the sequencing device 11. Although FIG. 5 illustrates a single adapter 571 or 572 per sequencing device 510 or 511, the system in FIG. 5 could also have multiple adapters per sequencing device, multiple sequencing devices per adapter, or multiple adapters interacting with multiple sequencing devices. For example, one adapter 571 proximate to the sequencing device 510 might include a license manager for authentication while the distal adapter 572 provides for command format conversion.

Adapters 571 or 572 can include one or more policies with rule sets established to govern the submission of commands and responses. The rule sets for the adapter 571 or 572 can manage timing issues, buffers, keys, tokens, pre-analysis instructions, commands, a priori knowledge base, and other elements in the genomic analysis system in FIG. 5.

Each class of adapter can target a different make or model of sequencing device. Moreover, it is contemplated that a heterogeneous mix of sequencing devices is capable of working with a single, common core analysis engine via a plurality of sequencing device adapters. The plurality of sequencing device adapters can be configured to target multiple sequencing devices. For example, adapter 571 can be configured to operate according to a common, normalized protocol format understood by analysis engine 500. Further, adapted 571 can comprise one or more conversion modules that convert from the common, normalized protocol to a device-specific protocol capable of being consumed by sequencing device 510.

Example instructions that can be submitted to the sequencing device 510 or 511 include instructions 501 to repeat (e.g., to increase sequencing depth of specific areas in a genome, or globally), halt, or start sequencing, or to coordinate parallel sequencing of same patient samples in different devices. The instructions 501 can also be instructions to send data, delete data, or prioritize sequencing. The instructions 501 can indicate that data should be forwarded or scheduled for sequencing. The instructions 501 can also include licensing management instructions. Further the instructions 501 can be derived based on a number of factors including patient data; healthcare provider; disease information; or other factors.

Distributed Genomic Storage Facilities

Figure 6:
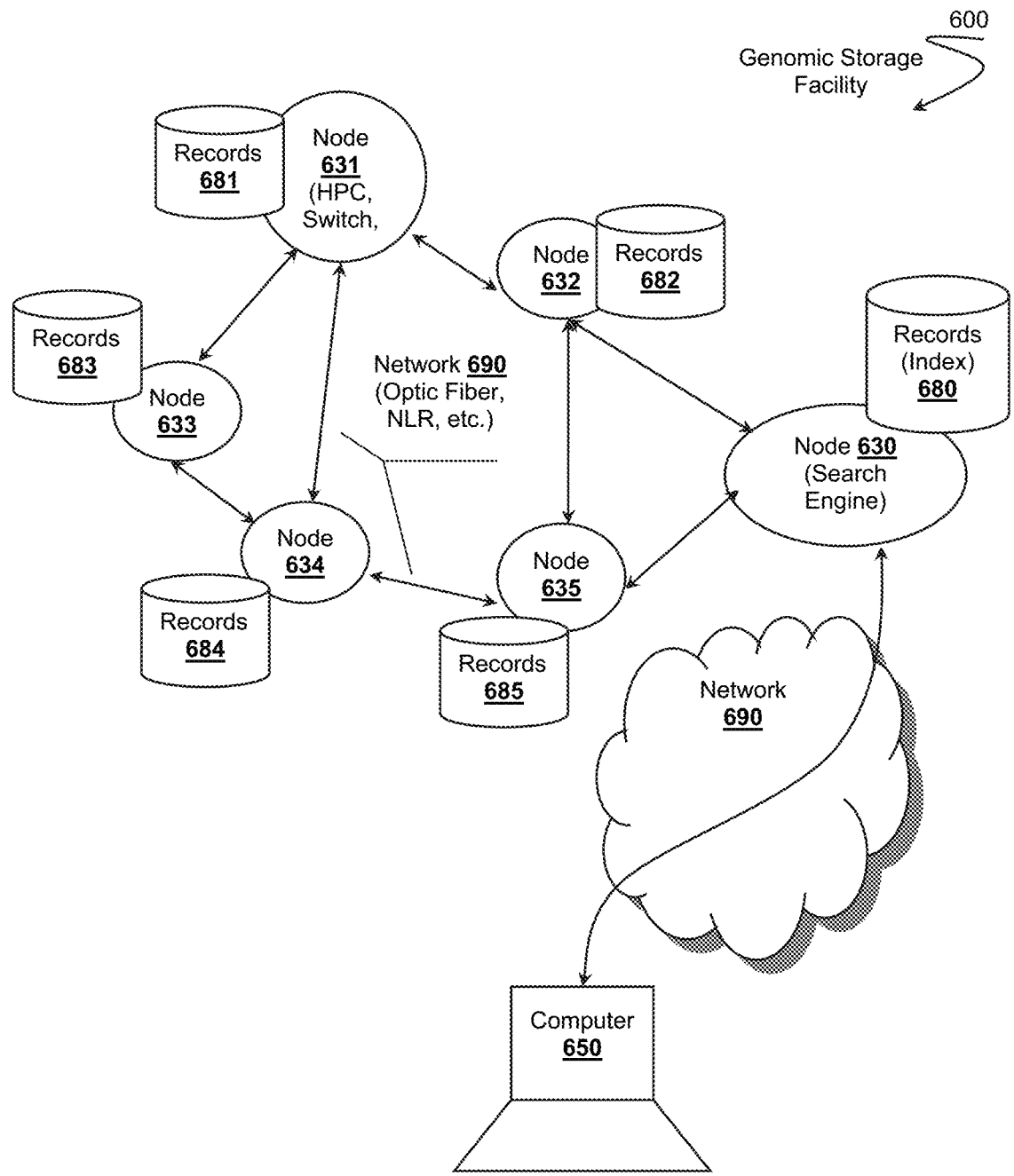
FIG. 6 is a schematic of a genomic storage facility.

FIG. 6 provides an illustration of a distributed genomic storage facility 600. In some embodiments, genomic records are stored in analysis nodes 630, 631, 632, 633, 634, or 635 associated with databases 680, 681, 682, 683, 684, or 685 or other facilities in a genomic analysis system 600 as illustrated. There are multiple genomics database repositories including but not limited to the National Center for Biotechnology Information (NCBI), European Molecular Biology Laboratory-European Bioinformatics Institute (EMBL-EBI), DNA Databank of Japan (DDBJ), International Nucleotide Sequence Database Collaboration (INSDC), NCBI Reference Sequence (RefSeq), the Vertebrate Genome Annotation Database (VEGA), Consensus coding sequences (CCDS), or other repositories.

The records stored in databases 680, 681, 682, 683, 684, or 685 can be stored according to any desired format. A record can be a whole genome; portions of the genome; sequences for genes or areas of concern (e.g., covering known SNPs, mutations, or other changes in the genome, including translocations and duplications); metadata (e.g., scientific and/or medial annotations for specific sequences); analysis results; comments by ordering physician, statistics; or other portions of the data. Preferably the records stored in 680, 681, 682, 683, 684, or 685 relate to a population of patients and enables research or analysis across demographics.

Records stored in records databases 680, 681, 682, 683, 684, or 685 can store differential data between genome data; differential data between a patient and a canonical human; differential data between a patient and a population. The reference or demographic factors can be based on a sample time, a tissue, a person, a gender, a family, a community, a demographic, a normalized sequence, a disease, a diet, an environment, an age, and other demographic factors. Most preferably, such differences are expressed in BAMBAM format and/or in a phylogenetic tree format.

Preferred embodiments include a genomic search engine 630; allowing users to submit queries to the engine 630. The search engine 630 finds matching records among the records databases 680, 681, 682, 683, 684, or 685, and the search engine 630 can be indexed by sequences or other factors and stored in a records index 680. The index for the distributed genomic database 600 can be based on many identifiers such as a patient identifier, a population identifier, a demographic, a disease, a diagnosis, a gender, an age, a location, an occupation, a risk factor, a sequence, a gene, a pathway, an allele, a prognosis, or other identifiers.

A query through the network 690 via a terminal such as a computer 650 to the search engine 630 of the records index 640 can take on a wide variety of forms. They can be a natural language query; a key words search; a sequences search; machine commands; APIs; or other forms of querying data.

Analysis Streams

The disclosed inventive subject matter presented thus far has mainly focused on genomic analysis stream management. However, one should appreciate that the disclosed continent spanning analysis stream management system can be applied to wider fields of care beyond genomic analysis. The reader should appreciate that the disclosed techniques leapfrogs over existing known genomic analysis by effectively constructing an integrated system of analysis engagement points that were previously impossible to combine.

Figure 7:
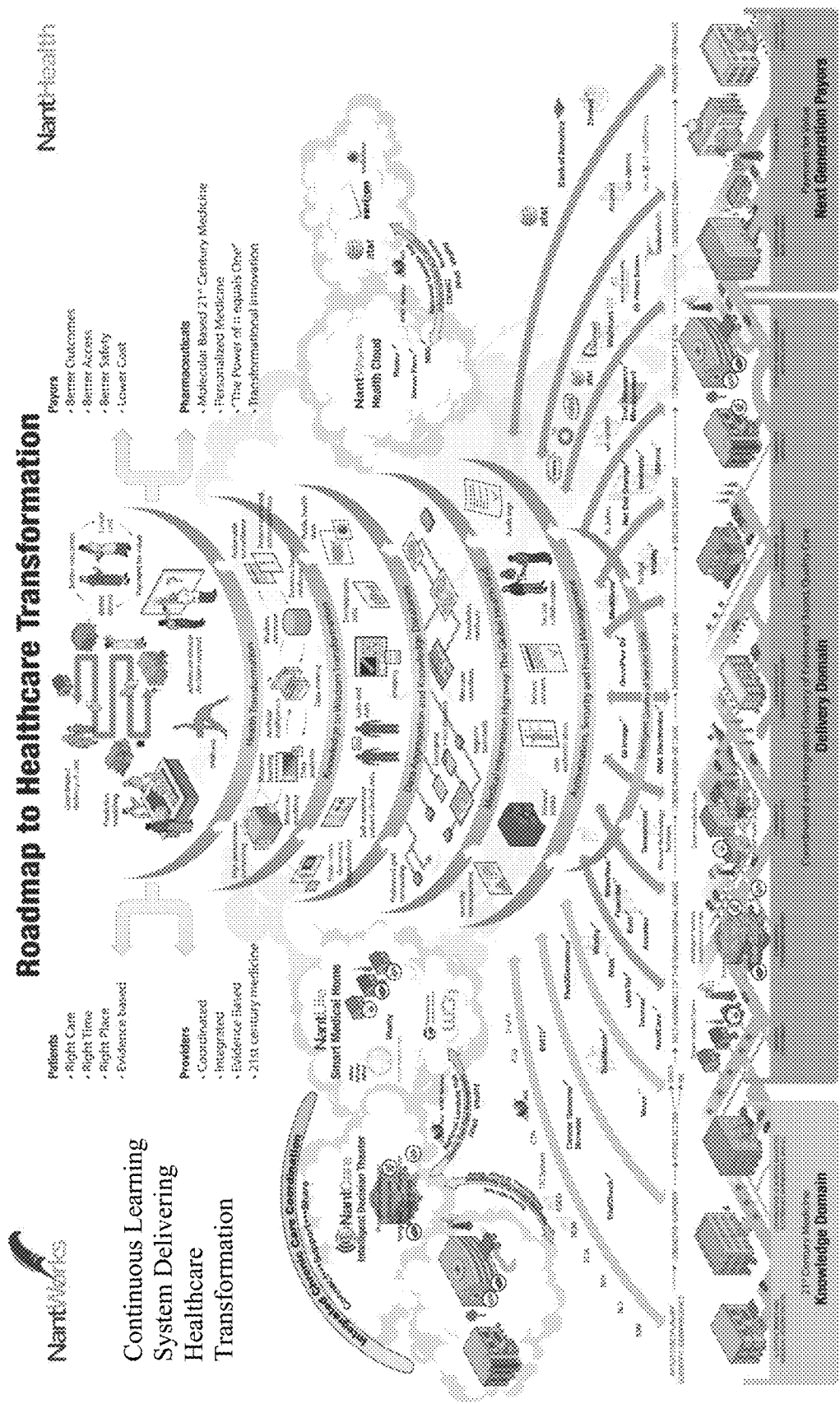
FIG. 7 is a schematic of a healthcare analysis stream management ecosystem.

FIG. 7 presents an over arching learning system capable of providing transformative healthcare. Analysis streams flow through the ecosystem as manageable computed-based objects among the engagement points. For example, a healthcare stream of data can be instrumented with analysis data from the elements of the knowledge domain (e.g., models, artificial intelligence, etc.). As an individual's healthcare stream is instantiated and populated with raw data (e.g., genomic information, biometrics, insurance plan data, etc.), the corresponding stream object can route the data to one or more proper analysis bodies that overlay or embedded corresponding analysis data (e.g., diagnosis, prognosis, recommendations, promotions, etc.).

The individual stream can then be considered an assembled human signal engine representative of the individual or even the individual's life. Thus the stream object can route the stream data through a delivery domain where the individual's stream data can be provided to healthcare provider networks, care facility, labs, pharmacies, hospices, or other entities. One should appreciate that each of the elements in the deliver domain can also augmented the data within the individual's healthcare stream.

As the individual's healthcare stream matures through development with respect to a specific topic (e.g., a specific disease state), or with respect to their over arching life, the stream object can then route data to outcome driven facility within the payor domain. Thus, the disclose stream management engines are able to direct relevant data directly to the stakeholders that are responsible for final disposition of the stream analysis. For example, the stream object can present an employer, a government, a financial institution, a benefit manager, or other entity with relative stream data.

Beyond genomics, the disclose ecosystem is capable of processing other types of stream data. For example, the disclosed analysis engines can also instrument an analysis stream with inferred proteomics (see Five3™ URL five3genomics(dot)com/technologies/paradigm), or actual quantitative proteomics (see OncoplexDx™ URL www(dot) oncoplexdx(dot)com). Still, further such data can be correlated with or tied one or more clinical protocol databases (see Eviti™ URL www(dot)eviti(dot)com) that coupled myriad of clinical protocols for many different cancer types, which are further combined with thousands of oncologists treating patients suffering from various disease states. One should appreciate that correlating the stream analysis nodes (e.g., PARADIGM, Oncoplex, etc.) with actual treatment and healthcare providers offers greater insight as a leading indicator of how best to care for individual's throughout their lives rather than after a disease state has occurred. Thus, an individual's healthcare analysis stream could start when they are born and possibly exist after death through binding with descendents. In a very real sense the disclosed ecosystem could be considered to give rise to "Care for Life", or more specifically with respect to cancer a stream-based "Cancer Care for Life".

In view that person's life can be represented as a cradle-to-grave stream object that directs stream data from analysis node to analysis node, one should appreciate that the disclosed system in aggregate learns, that is establish correlations or identify discoveries, about the person throughout their life. Thus, the system is capable of learning beyond the scope of a current disease state. A person's disease state, past, present or future, can also be correlated with other information including wellness imaging (see Qi Imaging™ at URL www(dot)qiimaging(dot)com) or including outcome level (see possibly net.orange™ see URL www(dot)ndorange(dot)com) with respect to "big data". Still further, the stream objects can be stored across generations of family managers where stream objects are cross correlated amongst contemporaneous family member or across generations. In such embodiments, the analysis streams provide for insight at the epigenetic level.

It should be appreciated by the reader that the integration among all dynamic elements illustrated in FIG. 7 gives rise to the ability to assess epigenetic effects across the life span of one or more analysis stream objects. For example, a real-time treatment protocol can be correlated with positive, negative, or neutral effects of the treatment with respect to a current analysis stream as well as analysis streams associated descendents. In some embodiments, the analysis stream objects can be consider epigenetic stream objects or even cross generational epigenetic stream objects.

The disclosed learning-based care for life, or even cancer care for life, analysis streams can be further augmented by data obtained with respect to more specific information, including specific genomic information. In some embodiments, sequencing devices can augment an analysis stream with sequence data representing double minutes, micro-RNA, genomic information related to circulating tumor cells, or other information. Such data can also be correlated across one or more analysis streams, especially epigenetic streams.

Analysis streams can also leverage biometric data, including integrating vital sign monitoring data into one or more analysis streams. As a person engages with one or more healthcare providers (e.g., a doctor's office, a hospital, ambulance, etc.), the healthcare provider often collects one or more points of data. In the past, over 99% of all data collected is discarded. In the disclosed ecosystem, all of the data can be stored or integrated into the person's healthcare analysis stream. For example, a patient's vital sign data can be collected via the iSirona™ DeviceConX™ technology, which can then be routed through an electronic medical record exchange. Further, the vital sign data can be bound to or integrated within an analysis stream object. Thus, the real-time vital sign data can be correlated (e.g., multi-variant analysis, factor analysis, inferences, etc.) with other stream related data. For example, real-time pulse oximeter data could be correlated with genomic data across one or more epigenetic stream objects.

Yet another aspect of the inventive subject matter is considered to include the formation of social networks based on analysis data derived from management of the streams within stream objects. As the streams associated with one or more stream objects pass through analysis nodes, the stream objects can be annotated with analysis profiles where the analysis profiles can be considered to represent possible healthcare contexts associated with the stream objects streams. The analysis engines can then offer recommendations to end users (e.g., patients, stakeholders, healthcare providers, service providers, payors, etc.) to join or instantiate social networks among each other based on similar profiles. As an example, consider a scenario where a group of patients have similar genomic profiles, possibly having similar phenotypic profiles, associated with a BRCA mutation. In response to the discovery, the analysis engines operating as a social network engine can instantiate a social network available to the patients or other stakeholders, through which the stakeholders can communicate or share experiences. The social networks can be instantiated as a common network or as individual, stand-along networks possibly depending on the nature of the molecular fingerprinting. Thus, the stream-based instantiated social networks could be open to the public, open only to those individuals exhibiting specific genomic profiles, or even restricted to only the stakeholders associated with a specific patient having a specific genomic profile. One should appreciate that the social network can provide for mutual support among patients, knowledge share among care providers, coordinated delivery among evidence-base care among stakeholders, decision support, home care integration, hospice support, or other types of continuous information exchange among stakeholders.

Although the previous social network example discussed the social network based on a healthcare environment, one should appreciate that the social networks can also support other activities including sharing of information based on or as a function of analysis profile information. For example, a person's like or dislikes could be correlated with genomic traits and could be shared with other having similar traits as recommendations. Consider a genomic-based social network where participants have had their "omic" (e.g., genomic, proteomic, pathways, etc.) information analyzed and have provided indications on which music, or other content, they like or dislike. The disclose analysis engines could attempt to establish correlations among music attributes with genomic traits. The engine could then offer music recommendations to other participants based on their traits. Yet another example could include matching people based on their genomic traits. For example, people could be matched together based complement traits, similar traits, or other traits. It should be appreciated that although the social networks reference healthcare, music and matching, the social networks can extend beyond such markets. Example additional genomic-based social networks could include gaming networks, shopping network, entertainment or entertaining networks (e.g., wine tasting, movie clubs, etc.), education or academic networks (e.g., tutoring, study groups, etc.), hobby networks, or other types of networks.

It should be appreciated that the Applicant has the unique capacity to deliver the above described system analysis management through existing relationships or partnerships with the referenced entities or technologies, and as evidenced by the experimental setups discussed above. Further, co-owned U.S. provisional applications 61/842,316, 61/842323, and 61/842,325 filed on Jul. 2, 2013, describe various aspects of healthcare management unified through healthcare analysis streams. For example, 61/842,323 discloses an energy balance representing a visual presentation of healthcare analysis stream data throughout a person's life. The energy balance is presented as a flower where each petal of the flower corresponds to one or more stream object metrics. Example metrics could represent activity level, sleep, nutrition, exercise, calories, risk of exposure to pathogens, or other stream data related to the person's corresponding stream object. The size, color, shape, or other petal attribute can represent aspects of the corresponding metrics. Green could indicate that the metric is in an acceptable range while red could indicate the metric is not acceptable.

Additional Considerations

The following tables present the above inventive subject matter from a claim perspective. Table 1 includes claims directed toward a sequencing system that includes a sequence device coupled with an add-on module configured to or programmed to allow the sequencing device to communicate a distributed genomic analysis system.

TABLE 1

Sequencing System with Add-on Modules

| Claims Number | Claim |
|---|---|
| 1 | A sequencing system comprising: a sequencing device capable of outputting raw sequence data; and an add-on module coupled with the sequencing device and configured to: pre-analyze the raw sequence data obtained from the sequencing device to generate a sequence annotation, assemble pre-analyzed sequence data from the raw sequence data and the sequence annotation, and forward the pre-analyzed sequence data to a sequence analysis facility. |
| 2 | The system of claim 1, wherein the sequence analysis facility comprises a remote high performance computing facility. |
| 3 | The system of claim 1, wherein the add-on module is further configured to forward the pre-analyzed sequence data according to the sequence annotation. |
| 4 | The system of claim 3, wherein the sequence annotation comprises processing parameters. |
| 5 | The system of claim 4, wherein the processing parameters comprises one or more of the following: routing parameters, analysis parameters, path parameters, destination parameters, source parameters, priority parameters, urgency parameters, class of service parameters, billing parameters, and payment parameters. |
| 6 | The system of claim 1, wherein the sequence annotation comprises sequence information. |
| 7 | The system of claim 6, wherein the sequence information comprises one or more of the following types of information: putative location, disease association, relative abundance information, gene association, class of nucleic acid, a chain of custody, and a tissue origin. |
| 8 | The system of claim 1, wherein the sequence annotation comprises patient information. |
| 9 | The system of claim 8, wherein the patient information comprises one or more of the following types of information: patient identifier, demographic information, geographic information, diagnostic information, healthcare provider information, intent of sequence analysis, account information, familial information, patient history, psychographic information, and germ line. |
| 10 | The system of claim 1, wherein the raw sequence data comprises genomic sequence data. |
| 11 | The system of claim 10, wherein the genomic sequence data represents a circular sequence. |
| 12 | The system of claim 1, wherein the raw sequence data comprises proteomic sequence data. |
| 13 | The system of claim 1, wherein the raw sequence data comprises RNA sequence data. |
| 14 | The system of claim 1, wherein the raw sequence data comprises small RNA sequence data. |
| 15 | The system of claim 1, wherein the raw sequence data comprises epigenetic sequence data. |
| 16 | The system of claim 1, wherein the add-on module further comprises a licensing manager. |

TABLE 1-continued

Sequencing System with Add-on Modules

| Claims Number | Claim |
|---|---|
| 17 | The system of claim 16, wherein the licensing manager is configured to authorize the add-on module to interact with the analysis facility. |
| 18 | The system of claim 16, wherein the licensing manager comprises one or more of the following: a subscription identifier, a number of uses, a licensing term, a permission level, an analysis account, and an analysis management module. |
| 19 | The system of claim 1, wherein the add-on module further comprises a sequence device controller. |
| 20 | The system of claim 19, wherein the sequence device controller submits sequence device commands to the sequence device. |
| 21 | The system of claim 20, wherein the sequence device commands are derived by the add-on module from instructions received from the analysis facility. |
| 22 | The system of claim 1, wherein the add-on module comprises a storage device controller that submits storage commands to a storage facility based on the pre-analyzed sequence data. |
| 23 | The system of claim 22, wherein the storage facility comprises at least one of the following: the sequence device, a memory of add-on module, a cloud storage system, and the analysis facility. |
| 24 | The system of claim 1, wherein the add-on module is configured to package the pre-analyzed sequence data according to a transfer format acceptable by the analysis facility. |
| 25 | The system of claim 1, wherein the add-on module comprises a hardware module configured to couple with a legacy sequence device operating as the sequence device. |
| 26 | The system of claim 1, wherein the sequence device comprises the add-on module. |
| 27 | The system of claim 26, wherein the sequence device integrates a non-transitory computer readable medium storing instructions comprising functionality of the add-on module. |
| 28 | The system of claim 1, wherein the analysis facility comprises the add-on module. |

Table 2 outlines a method for pre-processing raw sequence data where the pre-processed data can be forward to a genomic analysis facility.

TABLE 2

Pre-Processing of Sequence Data

| Claims Number | Claim |
|---|---|
| 1 | A method of pre-processing raw sequence data comprising: providing access to a pre-processing engine; providing access to an a priori knowledge base storing a priori known analysis-relevant information related to genomic data; receiving, by the pre-processing engine, raw genomic sequence data; pre-processing, by the pre-processing engine, the raw genomic sequence data using the a priori known analysis-relevant information to generate a sequence annotation; associating the sequence annotation with the raw sequence data to generate pre-processed sequence data; and forwarding the pre-processed sequence data to a sequence genomic analysis facility. |
| 2 | The method of claim 1, wherein the step of pre-processing includes roughly aligning raw reads within the sequence data against a course known genomic map within the a priori known analysis-relevant information to generate a rough alignment. |
| 3 | The method of claim 2, wherein the rough alignment comprises at least one of the following: position relative to a chromosome, position relative within a chromosome, association with a known allele, association with a known marker, and association with a known mutation. |
| 4 | The method of claim 2, wherein the sequence annotation comprises the rough alignment. |
| 5 | The method of claim 1, wherein the sequence annotation comprises at least one of the following: position in a genome, a known disease marker, a mutation, a diagnostic code, a procedural code, a billing code, analysis routing information, patient information, a demographic, a geographic coordinate, and a chain of custody. |
| 6 | The method of claim 1, wherein the sequence annotation comprises a suspected diagnosis. |

TABLE 2-continued

Pre-Processing of Sequence Data

| Claims Number | Claim |
|---|---|
| 7 | The method of claim 1, wherein the sequence annotation comprises an analysis prioritization. |
| 8 | The method of claim 7, wherein the analysis prioritization includes an analysis weighting based at least in part on the a priori known analysis-relevant information. |
| 9 | The method of claim 1, wherein the sequence annotation comprises an alert trigger. |
| 10 | The method of claim 1, wherein the step of pre-processing includes pre-processing in-band with the analysis facility. |
| 11 | The method of claim 10, wherein the step of pre-processing includes pre-processing substantially in real-time with reception of the raw sequence data. |

Table 3 presents a sequence analysis system where a genomic analysis engine is able to interactively work with sequencing devices through bi-direction exchanges to manage a genomic analysis stream. The sequencing devices can leverage one or more adapters.

TABLE 3

Interactive Sequencing among Analysis Engines and Sequencing Devices

| Claims Number | Claim |
|---|---|
| 1 | An sequence analysis system comprising: at least one analysis engine configured to analyze sequence data; at least one sequencing device adapter coupled with the at least one analysis engine and configured to bi-directionally exchange data between the at least one analysis engine and a target sequencing device; and wherein the analysis engine is further configured to submit sequencing instructions to the target sequencing device via the sequencing device adapter. |
| 2 | The system of claim 1, wherein the sequence data comprises pre-processed sequence data. |
| 3 | The system of claim 1, wherein the sequencing instructions are submitted over a network. |
| 4 | The system of claim 3, wherein the network comprises an optic fiber network. |
| 5 | The system of claim 1, wherein the sequencing instructions comprise at least one of the following: repeat sequencing target sequence area, halt sequencing, start sequencing, send data upon satisfaction of a trigger, delete sequence data from sequencing device, licensing management instructions, prioritizing sequence events, forwarding instructions of sequence data, and scheduling sequencing. |
| 6 | The system of claim 1, wherein the sequencing instructions are based at least in part on patient information. |
| 7 | The system of claim 1, wherein the sequencing instructions are based at least in part on disease information. |
| 8 | The system of claim 1, wherein the analysis engine comprises a distributed analyses engine having a plurality of analysis nodes. |
| 9 | The system of claim 8, wherein at least two analysis nodes are geographically distributed. |
| 10 | The system of claim 1, wherein the at least one sequencing device adapter comprises a plurality of sequencing device adapters where each adapter targets a different type of sequencing machine. |
| 11 | The system of claim 10, wherein the plurality of sequencing device adapters target at least 10 target sequencing devices. |
| 12 | The system of claim 11, wherein the plurality of sequencing device adapters target at least 100 target sequencing devices. |

Table 4 presents a genomic storage facility having a distributed data and a genomic search engine. As discussed previously, there are multiple issues that hinder an ability to (1) rapidly transport big genomic data to processing and storage computers located at centralized data centers, (2) accurately assess all of the variances found in the DNA of a patient's cancer tissue, (3) identify the many clones in a heterogeneous disease such as cancer, and (4) predict the systemic impact of each variance of each clone on the cellular signaling pathways. The disclosed distributed system provides for massive scaling of deriving actionable information. Further, the applicants have successfully demonstrated the ability overcome all four barriers and an ability to predict the right treatment for the right patient at the right time. As a demonstration of speed and continental outreach, the applicant's experiments resulted in the 700 mile transport, processing, and mutational analysis of 6,000 exomes in 69 hours or 82 seconds per patient. Transport was facilitated by the National LambdaRail, the 12,000 mile optical fiber network that excels at rapidly and robustly transporting bandwidth-crushing data across hospitals, clinics, and universities across the U.S.

TABLE 4

Distributed Genomic Storage Facility

| Claims Number | Claim |
|---|---|
| 1 | A genomic storage facility comprising: a distributed genomic database storing genome data records associated with genomic data of a population of patients; and a genomic search engine coupled with the distributed genomic database and configured to return genome data records from the genomic data in response to a query. |
| 2 | The facility of claim 1, wherein the distributed genomic database comprises memory distributed among genomic analysis nodes over a network. |
| 3 | The facility of claim 2, wherein the network comprises an optic fiber network. |
| 4 | The facility of claim 3, wherein the network comprises a geographically distributed optic fiber network. |
| 5 | The facility of claim 2, wherein the genomic analysis nodes comprise high performance computing facilities. |
| 6 | The facility of claim 1, wherein the genome data comprises differences between a patient's sequence and a reference sequence. |
| 7 | The facility of claim 6, wherein the differences are with respect to at least one of the following: a sample time, a tissue, a person, a gender, a family, a community, a demographic, a normalized sequence, a disease, a diet, an environment, and an age. |
| 8 | The facility of claim 1, wherein the population of patients comprises at least 100 patients. |
| 9 | The facility of claim 8, wherein the population of patients comprises at least 1000 patients. |
| 10 | The facility of claim 9, wherein the population of patients comprises at least 10000 patients. |
| 11 | The facility of claim 1, wherein the distributed genomic database is indexed by at least one of the following: a patient identifier, a population identifier, a demographic, a disease, a diagnosis, a gender, a location, an occupation, a risk factor, a sequence, a gene, a pathway, and an allele. |
| 12 | The facility of claim 1, wherein the query comprises a natural language query. |
| 13 | The facility of claim 1, wherein the query comprises a machine query. |

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A genomic analysis system comprising:
a sequencing device interface configured to acquire sequence data from a plurality of sequencing devices, where the sequence data is from a plurality of patients;
an analysis network; and
a plurality of analysis computer nodes interconnected via the analysis network forming a genomic analysis engine having patient-specific analysis network topologies coupled with the sequencing device interface, and configured to process the sequence data from the patients in parallel into patient-specific genome data according to processing routes of the patient-specific analysis network topologies wherein different analysis computer nodes execute on different processors.

2. The system of claim 1, wherein the analysis engine is configured to process sequence data from at least 10 patients in parallel.

3. The system of claim 1, wherein the analysis engine is configured to process sequence data into the genome data at a rate of at least X patients per Y unit of time, where X is at least 3 and Y is at most one day.

4. The system of claim 3, wherein X at least is ten and Y is at most one hour.

5. The system of claim 3, wherein X is at least ten and Y is at most one day.

6. The system of claim 1, wherein the analysis network comprises an optic fiber data link.

7. The system of claim 6, wherein the analysis network comprises a continent spanning network.

8. The system of claim 1, wherein the sequencing device interface is configured to obtain the sequence data from at least 100 sequencing devices in parallel.

9. The system of claim 1, wherein the genome data comprises genomic data associated with a demographic of the patients.

10. The system of claim 1, wherein the analysis engine is configured to generate a notification as a function of the genome data, and wherein the notification comprises at least one of the following: a processing status, an analysis engine management status, an alert, an alarm, a sequencing device instruction, an analysis recommendation, a prognosis, a diagnosis, and an inter-node communication.

11. The system of claim 1, wherein the analysis engine is configured to generate a notification as a function of the genome data, wherein the notification configures a route within the analysis network, and wherein the route allows the notification to be sent to at least one of the following: a point-of-care, a sequencing device, a patient, and a healthcare service provider.

12. The system of claim 1, further comprising an engine management node configured to manage the analysis engine.

13. The system of claim 12, wherein the engine management node is configured to generate an analysis dashboard.

14. The system of claim 12, wherein the engine management node is configured to transmit an analysis status to a user.

15. The system of claim 1, wherein the analysis computer nodes comprise network switches.

16. The system of claim 1, wherein each of the analysis stream objects comprises an analysis data stream of the sequence data through processing to the genome data.

17. The system of claim 16, wherein the analysis data stream extends from a sequencing device through the sequencing device interface and through the analysis engine to an output device.

18. The system of claim 1, wherein the analysis stream object comprises at least one analysis route applied to the sequence data.

19. The system of claim 1, wherein the at least one stream management functionality comprises one of the following: modifying an analysis route, instantiating an analysis stream according to the stream object, conducting a transaction based on the analysis stream object, altering an analysis, constructing notification trigger criteria based on the analysis stream object, and deconstructing an analysis stream.

20. The system of claim 1, wherein the sequencing device interface is configured to acquire sequence data through an image recognition algorithm applied to image data representing the sequence data, and wherein the image recognition algorithm operates as a function of a scale invariant feature transform.

21. The system of claim 1, wherein the sequencing device interface is configured to acquire sequence data through an image recognition algorithm applied to image data representing the sequence data, and wherein the sequencing device is further configured to translate the image data into a DNA base via serial time encoded amplified microscopy (STEAM).

22. The system of claim 1, wherein the analysis engine is configured to acquire sequence data through an image recognition algorithm applied to image data representing the sequence data, and wherein the image recognition algorithm operates as a function of a scale invariant feature transform.

23. The system of claim 1, wherein the analysis engine is configured to acquire sequence data through an image recognition algorithm applied to image data representing the sequence data, wherein the analysis engine is further configured to translate the image data into a DNA base via serial time encoded amplified microscopy (STEAM).

24. A genomic analysis apparatus, the apparatus comprising:
an analysis computer node interconnected to a plurality of analysis computer nodes via an analysis network forming a genomic analysis engine having patient-specific analysis network topologies coupled with a sequencing device interface, and configured to process sequence data from patients in parallel into patient-specific genome data according to processing routes of the patient-specific analysis network topologies wherein different analysis computer nodes execute on different processors.

25. A genomic analysis method, the method comprising:
receiving sequence data from a plurality of sequencing devices, wherein the sequence data corresponds to a plurality of patients; and
configuring an analysis network having a plurality of analysis computer nodes to form patient-specific analysis network topologies of a genomic analysis engine that processes the sequence data from the patients in parallel into patient-specific genome data according to processing routes of the patient-specific analysis network topologies wherein different analysis computer nodes execute on different processors.

* * * * *